(12) United States Patent
Simmen et al.

(10) Patent No.: US 8,008,251 B2
(45) Date of Patent: Aug. 30, 2011

(54) MACROCYCLIC INHIBITORS OF HEPATITIS C VIRUS

(75) Inventors: Kenneth Alan Simmen, Tervuren (BE); Herman Augustinus De Kock, Arendonk (BE); Pierre Jean-Marie Bernard Raboisson, Sterrebeek (BE); Mats Stefan Lindström, Huddinge (SE); Pia Cecilia Kahnberg, Huddinge (SE); Dmitry Antonov, Huddinge (SE); Karl Magnus Nilsson, Huddinge (SE); Bengt Bertil Samuelsson, Huddinge (SE); Åsa Annica Kristina Rosenquist, Huddinge (SE)

(73) Assignees: Tibotec Pharmaceuticals Ltd. (IE); Medivir AB (SE)

( * ) Notice: Subject to any disclaimer, the term of this patent is extended or adjusted under 35 U.S.C. 154(b) by 326 days.

(21) Appl. No.: 11/995,888

(22) PCT Filed: Jul. 28, 2006

(86) PCT No.: PCT/EP2006/064812
§ 371 (c)(1),
(2), (4) Date: Jan. 16, 2008

(87) PCT Pub. No.: WO2007/014918
PCT Pub. Date: Feb. 8, 2007

(65) Prior Publication Data
US 2008/0200503 A1    Aug. 21, 2008

(30) Foreign Application Priority Data

Jul. 29, 2005  (EP) ..................... 05107066
Feb. 3, 2006   (EP) ..................... 06101278

(51) Int. Cl.
A61K 38/05 (2006.01)
C07K 5/078 (2006.01)
(52) U.S. Cl. ............... 514/4.3; 514/21.1; 514/21.91; 540/460
(58) Field of Classification Search .............. None
See application file for complete search history.

(56) References Cited

U.S. PATENT DOCUMENTS

| | | | |
|---|---|---|---|
| 5,484,801 A | 1/1996 | Al-Razzak | |
| 5,807,876 A | 9/1998 | Armistead et al. | |
| 5,948,436 A | 9/1999 | Venkat | |
| 6,037,157 A | 3/2000 | Norbeck et al. | |
| 6,054,472 A | 4/2000 | Armistead et al. | |
| 6,344,465 B1 | 2/2002 | Armistead et al. | |
| 6,498,178 B2 | 12/2002 | Stamos et al. | |
| 6,867,185 B2 * | 3/2005 | Campbell et al. | 514/9 |

FOREIGN PATENT DOCUMENTS

| | | |
|---|---|---|
| WO | WO 94/14436 | 7/1994 |
| WO | WO 95/07696 | 3/1995 |
| WO | WO 95/09614 | 4/1995 |
| WO | WO 97/40028 | 10/1997 |
| WO | WO 98/17679 | 4/1998 |
| WO | WO 98/22496 | 5/1998 |
| WO | WO 98/40381 | 9/1998 |
| WO | WO 99/07734 | 2/1999 |
| WO | WO 00/09543 | 2/2000 |
| WO | WO 00/56331 | 9/2000 |
| WO | WO 00/59929 | 10/2000 |
| WO | WO 02/18369 | 3/2002 |
| WO | WO 03/087092 | 10/2003 |
| WO | WO 2005/073195 | 8/2005 |
| WO | WO 2005/073216 | 8/2005 |

OTHER PUBLICATIONS

Bodanszky, M., "Peptide Chemistry", 2$^{nd}$ Red. Ed., Springer-Verlag, Berlin, Germany (1993). Title Page and Table of Contents.
Goodman and Gillman's "The Pharmacological Basis of Therapeutics" Eighth Edition, McGraw-Hill, Inc., Health Professions Division, p. 1-20 (Title Page and Table of Contents), (1991).
Greene, "Protective Groups in Organic Chemistry", Wiley & Sons, NY (1999) "The Peptides: Analysis, Synthesis, Biology", vol. 9, Academic Press, NY (1987) (Title Page and Table of Contents).

(Continued)

*Primary Examiner* — Jeffrey E Russel

(57) ABSTRACT

Inhibitors of HCV of formula (I).

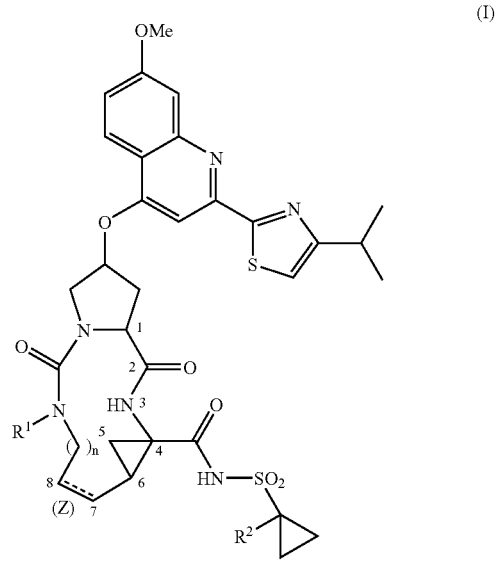

and the N-oxides, salts, and stereoisomers thereof, wherein the dashed line represents an optional double bond between atoms C7 and C8; $R^1$ is hydrogen or $C_{1-6}$alkyl; $R^2$ is hydrogen or $C_{1-6}$alkyl; and n is 3, 4, 5, or 6;
pharmaceutical compositions containing compounds (I) and processes for preparing compounds (I) are provided. Bioavailable combinations of the inhibitors of HCV of formula (I) with ritonavir are also provided.

15 Claims, No Drawings

OTHER PUBLICATIONS

Huang, et al., "Olefin Metathesis-Active Ruthenium Complexes Bearing a Nucleophilic Carbene Ligand" J. Am. Chem. Soc. 1999 121, p. 2674-2678.

Kingsbury, J., "A Recyclable Ru-Based Metathesis Catalyst", et al., J. Am. Chem. Soc. 1999, 121, p. 791-799.

Krchnak, V. et al., "Polymer-Supported Mitsunobu Ether Formation and its Use in Combinatorial Chemistry", Tetrahedron Letters, vol. 36, No. 35, p. 6193-6195, 1995.

Krieger, N., et al., "Enhancement of Hepatitis C Virus RNA Replication by Cell Culture-Adaptive Mutations", Journal of Virology, May 2001, pp. 4614-4624.

Liu, Y., et al. "Use of a Fluorescence Plate Reader for Measuring Kinetic Parameters with Inner Filter Effect Correction", Analytical Biochemistry 267, pp. 331-335 (1999).

Lohmann, V., et al., "Replication of Subgenomic Hepatitis C Virus RNAs in a Hepatoma Cell Line", Science 285, 1999, pp. 110-113.

Miller, S., et al., "Application of Ring-Closing Metathesis to the Synthesis of Rigidified Amino Acids and Peptides", J. Am. Chem. Soc. 1996, 118, p. 9606-9614.

Mitsunobu, O., "The Use of Diethyl Azodicraboxylate and Triphenylphosphine in Synthesis and Transformation of Natural Products", Synthesis, Jan. 1-28, 1981.

Rano, T. et al., "Solid Phase Synthesis of Aryl Ethers via the Mitsunobu Reaction", Tetrahedron Letters, vol. 36, No. 22, pp. 3789-3792, 1995.

Richter, L. et al, "A Surprising Observation about Mitsunobu Reactions in Solid Phase Synthesis", Tetrahedron Letters, vol. 35, No. 27, p. 4705-4706, 1994.

Hou, Tingjun et al. "pharmacophore Model and 3D-QSAR study of two kinds of HCV NS3 Serine protease Inhibitiors", Acta Physico-Chimica Sinica, vol. 16, No. 3, pp. 196-201 (2000).

Landro, "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, vol. 36, pp. 9340-9348 (1997).

Poliakov, "Expression and Purification of Recombinant Full-Length NS3 Protease-Helicase from a New Variant of Hepatitis C Virus", Protein Expression and Purification, vol. 25, pp. 363-371 (2002).

Smith, E.M., et al. "Synthesis and Pharmacological Activity of Angiotensin Converting Enzyme Inhibitors: N-(Mercaptoacyl)-4-substituted-(S)-prolines" Journal of Medicinal Chemistry, vol. 31, pp. 875-885 (1988).

* cited by examiner

MACROCYCLIC INHIBITORS OF HEPATITIS C VIRUS

CROSS REFERENCE TO RELATED APPLICATIONS

This application claims priority of the benefits of the filing of Patent Application No. EP 05107066.2 filed Jul. 29, 2005; EP 06101278.7 filed Feb. 3, 2006; and PCT Application No. PCT/EP2006/064812 filed Jul. 28, 2006. The complete disclosures of the aforementioned related patent applications are hereby incorporated herein by reference for all purposes.

The present invention is concerned with macrocyclic compounds having inhibitory activity on the replication of the hepatitis C virus (HCV). It further concerns compositions comprising these compounds as active ingredients as well as processes for preparing these compounds and compositions.

Hepatitis C virus is the leading cause of chronic liver disease worldwide and has become a focus of considerable medical research. HCV is a member of the Flaviviridae family of viruses in the hepacivirus genus, and is closely related to the flavivirus genus, which includes a number of viruses implicated in human disease, such as dengue virus and yellow fever virus, and to the animal pestivirus family, which includes bovine viral diarrhea virus (BVDV). HCV is a positive-sense, single-stranded RNA virus, with a genome of around 9,600 bases. The genome comprises both 5' and 3' untranslated regions which adopt RNA secondary structures, and a central open reading frame that encodes a single polyprotein of around 3,010-3,030 amino acids. The polyprotein encodes ten gene products which are generated from the precursor polyprotein by an orchestrated series of co- and posttranslational endoproteolytic cleavages mediated by both host and viral proteases. The viral structural proteins include the core nucleocapsid protein, and two envelope glycoproteins E1 and E2. The non-structural (NS) proteins encode some essential viral enzymatic functions (helicase, polymerase, protease), as well as proteins of unknown function. Replication of the viral genome is mediated by an RNA-dependent RNA polymerase, encoded by non-structural protein 5b (NS5B). In addition to the polymerase, the viral helicase and protease functions, both encoded in the bifunctional NS3 protein, have been shown to be essential for replication of HCV RNA. In addition to the NS3 serine protease, HCV also encodes a metalloproteinase in the NS2 region.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis leading to cirrhosis, end-stage liver disease, and HCC (hepatocellular carcinoma), making it the leading cause of liver transplantations.

There are 6 major HCV genotypes and more than 50 subtypes, which are differently distributed geographically. HCV type 1 is the predominant genotype in Europe and the US. The extensive genetic heterogeneity of HCV has important diagnostic and clinical implications, perhaps explaining difficulties in vaccine development and the lack of response to therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV type 1, this combination therapy has significant side effects and is poorly tolerated in many patients. Major side effects include influenza-like symptoms, hematologic abnormalities, and neuropsychiatric symptoms. Hence there is a need for more effective, convenient and better tolerated treatments.

Recently, two peptidomimetic HCV protease inhibitors have gained attention as clinical candidates, namely BILN-2061 disclosed in WO00/59929 and VX-950 disclosed in WO03/87092. A number of similar HCV protease inhibitors have also been disclosed in the academic and patent literature. It has already become apparent that the sustained administration of BILN-2061 or VX-950 selects HCV mutants which are resistant to the respective drug, so called drug escape mutants. These drug escape mutants have characteristic mutations in the HCV protease genome, notably D168V, D168A and/or A156S. Accordingly, additional drugs with different resistance patterns are required to provide failing patients with treatment options, and combination therapy with multiple drugs is likely to be the norm in the future, even for first line treatment.

Experience with HIV drugs, and HIV protease inhibitors in particular, has further emphasized that sub-optimal pharmacokinetics and complex dosage regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design. The strong peptidomimetic nature of prior art HCV protease inhibitors, with multiple peptide bonds poses pharmacokinetic hurdles to effective dosage regimes.

There is a need for HCV inhibitors which may overcome the disadvantages of current HCV therapy such as side effects, limited efficacy, the emerging of resistance, and compliance failures.

The present invention concerns HCV inhibitors which are superior in one or more of the following pharmacological related properties, i.e. potency, decreased cytotoxicity, improved pharmacokinetics, improved resistance profile, acceptable dosage and pill burden.

The present invention concerns inhibitors of HCV replication, which can be represented by formula (I):

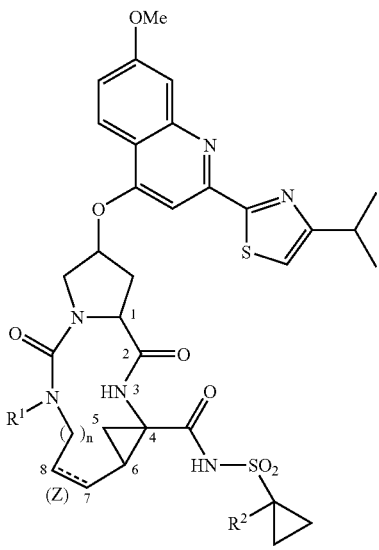

(I)

and the N-oxides, salts, and stereoisomers thereof, wherein the dashed line represents an optional double bond between atoms C7 and C8;

$R^1$ is hydrogen or $C_{1-6}$alkyl;

$R^2$ is hydrogen or $C_{1-6}$alkyl; and n is 3, 4, 5, or 6.

The present invention concerns two subgroups of inhibitors of HCV replication, which can be represented by formula (I-a) and (I-b):

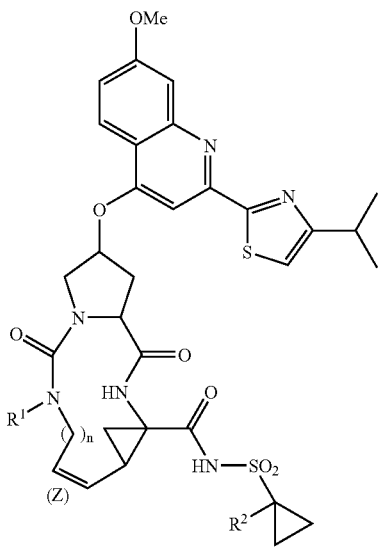

(I-a)

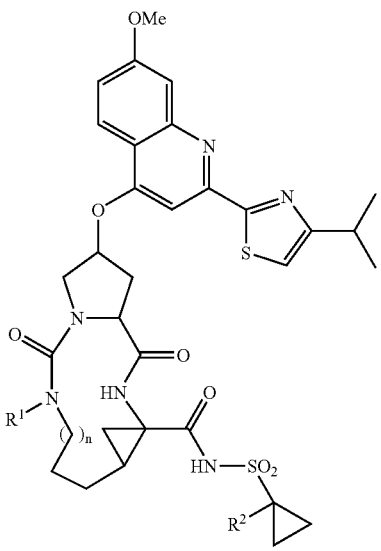

(I-b)

and the N-oxides, salts, and stereoisomers thereof, wherein $R^1$, $R^2$ and n are as defined herein.

The invention further relates to methods for the preparation of the compounds of formula (I), the N-oxides, addition salts, quaternary amines, metal complexes, and stereochemically isomeric forms thereof, its intermediates, and the use of the intermediates in the preparation of the compounds of formula (I).

The invention relates to the compounds of formula (I) per se, the N-oxides, addition salts, quaternary amines, metal complexes, and stereochemically isomeric forms thereof, for use as a medicament. The invention further relates to pharmaceutical compositions comprising a carrier and an antivirally effective amount of a compound of formula (I) as specified herein. The pharmaceutical compositions may comprise combinations of the aforementioned compounds with other anti-HCV agents. The invention further relates to the aforementioned pharmaceutical compositions for administration to a subject suffering from HCV infection.

The invention also relates to the use of a compound of formula (I), or a N-oxide, addition salt, quaternary amine, metal complex, or stereochemically isomeric forms thereof, for the manufacture of a medicament for inhibiting HCV replication. Or the invention relates to a method of inhibiting HCV replication in a warm-blooded animal said method comprising the administration of an effective amount of a compound of formula (I), or a N-oxide, addition salt, quaternary amine, metal complex, or stereochemically isomeric forms thereof.

As used in the foregoing and hereinafter, the following definitions apply unless otherwise noted.

As used herein "$C_{1-6}$alkyl" as a group or part of a group defines straight or branched chain saturated hydrocarbon radicals having from 1 to 6 carbon atoms such as for example methyl, ethyl, 1-propyl, 2-propyl, 1-butyl, 2-butyl, 2-methyl-1-propyl, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_{1-6}$alkyl is $C_{1-4}$alkyl.

Whenever used hereinafter, the term "compounds of formula (I)", or "the present compounds" or similar terms, it is meant to include the compounds of formula (I), each and any of the subgroups thereof, their prodrugs, N-oxides, addition salts, quaternary amines, metal complexes, and stereochemically isomeric forms. One embodiment comprises the compounds of formula (I) or any subgroup of compounds of formula (I) specified herein, as well as the N-oxides, salts, as the possible stereoisomeric forms thereof. Another embodiment comprises the compounds of formula (I) or any subgroup of compounds of formula (I) specified herein, as well as the salts as the possible stereoisomeric forms thereof.

The compounds of formula (I) have several centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I) may possess.

With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl-tartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds of formula (I) can be obtained separately by conventional methods. Appropriate physical separation methods that may advantageously be employed are, for example, selective crystallization and chromatography, e.g. column chromatography.

For some of the compounds of formula (I), their N-oxides, salts, solvates, quaternary amines, or metal complexes, and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmaco-logical Basis of Therapeutics, 8$^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) having a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$alkoxymethyl esters for example methoxy-methyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyl-oxyethyl which may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxy-methoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

For therapeutic use, salts of the compounds of formula (I) are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkyl halide, aryl halide or arylalkyl halide, e.g. methyl iodide or benzyl iodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complex forming properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

As mentioned above, the compounds of formula (I) have several asymmetric centers. In order to more efficiently refer to each of these asymmetric centers, the numbering system as indicated in the following structural formula will be used.

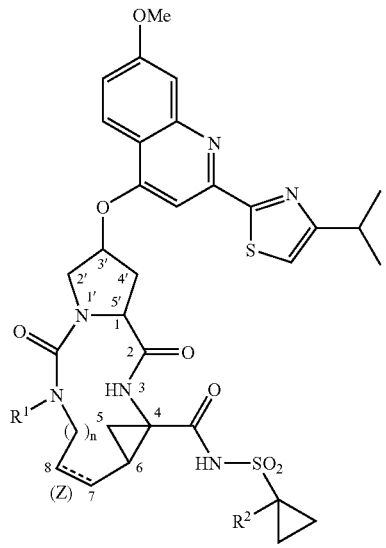

(I)

Asymmetric centers are present at positions 1, 4 and 6 of the macrocycle as well as at the carbon atom 3' in the pyrrolidine ring. Each of these asymmetric centers can occur in their R or S configuration.

The stereochemistry at position 1 preferably corresponds to that of an L-amino acid configuration, i.e. that of L-proline.

The compounds of formula (I) include a cyclopropyl group as represented in the structural fragment below:

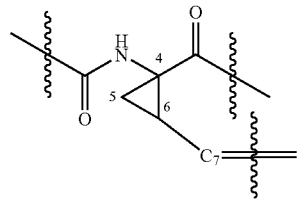

wherein $C_7$ represents the carbon at position 7 and carbons at position 4 and 6 are asymmetric carbon atoms of the cyclopropane ring.

Notwithstanding other possible asymmetric centers at other segments of the compounds of the invention, the presence of these two asymmetric centers means that the compounds can exist as mixtures of diastereomers, such as the diastereomers of compounds of formula (I) wherein the carbon at position 7 is configured either syn to the carbonyl or syn to the amide as shown below.

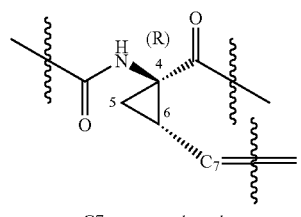

C7 syn to carbonyl

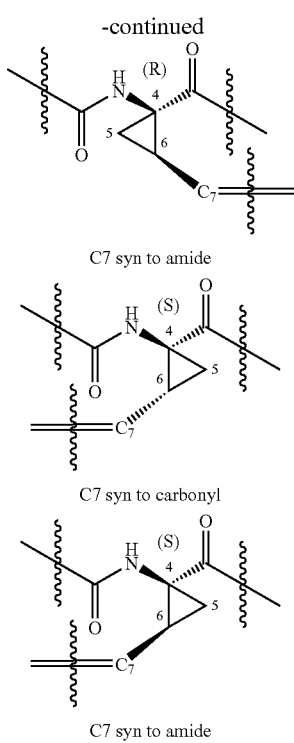

C7 syn to amide

C7 syn to carbonyl

C7 syn to amide

One embodiment concerns compounds of formula (I) wherein the carbon at position 7 is configured syn to the carbonyl. Another embodiment concerns compounds of formula (I) wherein the configuration at the carbon at position 4 is R. A specific subgroup of compounds of formula (I) are those wherein the carbon at position 7 is configured syn to the carbonyl and wherein the configuration at the carbon at position 4 is R.

The compounds of formula (I) also include a proline residue. Preferred are the compounds of formula (I) wherein the substituent at the 1 (or 5') position and the substituent at position 3' are in a trans configuration. Of particular interest are the compounds of formula (I) wherein position 1 has the configuration corresponding to L-proline and the substituent at position 3' is in a trans configuration in respect of position 1. Preferably the compounds of formula (I) have the stereochemistry as indicated in the structure of formula (I-c) below:

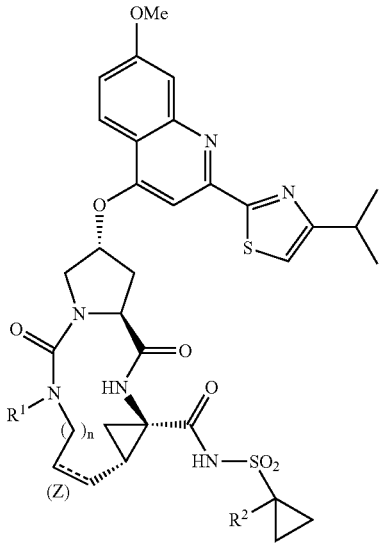

(I-c)

Preferably, the dashed line is a double bond between carbon atoms 7 and 8 in the compounds of formula (I), (I-c) or in any subgroup of compounds of formula (I). More preferably said double bond between carbon atoms 7 and 8 is in a cis configuration.

It is to be understood that the above defined subgroup of compounds of formulae (I-b), as well as any other subgroup defined herein, are meant to also comprise any N-oxides, addition salts, quaternary amines, metal complexes and stereochemically isomeric forms of such compounds.

When n is 2, the moiety —$CH_2$— bracketed by "n" corresponds to ethanediyl in the compounds of formula (I) or in any subgroup of compounds of formula (I). When n is 3, the moiety —$CH_2$— bracketed by "n" corresponds to propanediyl in the compounds of formula (I) or in any subgroup of compounds of formula (I). When n is 4, the moiety —$CH_2$— bracketed by "n" corresponds to butanediyl in the compounds of formula (I) or in any subgroup of compounds of formula (I). When n is 5, the moiety —$CH_2$-bracketed by "n" corresponds to pentanediyl in the compounds of formula (I) or in any subgroup of compounds of formula (I). When n is 6, the moiety —$CH_2$— bracketed by "n" corresponds to hexanediyl in the compounds of formula (I) or in any subgroup of compounds of formula (I). Particular subgroups of the compounds of formula (I) are those compounds wherein n is 4 or 5.

Preferred embodiments of the invention are compounds of formula (I) or any of the subgroups of compounds of formula (I) wherein $R^1$ is hydrogen or methyl.

Embodiments of the invention are those compounds of formula (I) or any of the subgroups of compounds of formula (I) wherein $R^2$ is hydrogen, or $C_{1-4}$alkyl, i.e. methyl, ethyl, propyl, isopropyl, butyl, tert-butyl, or isobutyl.

A subgroup of compounds of the invention are those compounds of formula (I) or any of the subgroups of compounds of formula (I) wherein $R^2$ is hydrogen.

Another subgroup of compounds of the invention are those compounds of formula (I) or any of the subgroups of compounds of formula (I) wherein $R^2$ is methyl.

The compounds of formula (I) consist of three main building blocks P1, P2, and P3, which are each delimited by a curved sinusoidal line. The building block P1 further contains a P1' tail. The carbonyl group marked with an asterisk may be part of either building block P2 or of building block P3. The linking of building blocks P1 with P2, P2 with P3, and P1 with P1', involve forming an amide bond. The linking of blocks P1 and P3 involves a double bond formation. The linking of building blocks P1, P1', P2 and P3 to prepare compounds of formula (I) can be done in any given sequence. One of the steps involves a cyclization whereby the macrocycle is formed.

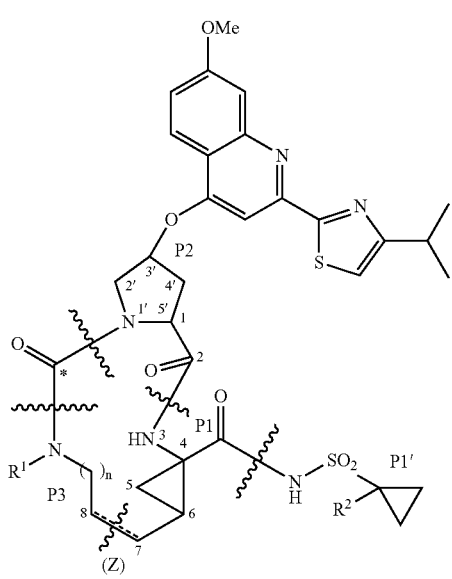

(I)

The synthesis procedures described hereinafter are meant to be applicable for as well the racemates, stereochemically pure intermediates or end products, as any stereoisomeric mixtures. The racemates or stereochemical mixtures may be separated into stereoisomeric forms at any stage of the synthesis procedures. In one embodiment, the intermediates and end products have the stereochemistry specified above in the compounds of formula (I-c).

In one embodiment, compounds (I) are prepared by first forming the amide bonds and subsequent forming the double bond linkage between P3 and P1 with concomitant cyclization to the macrocycle.

In a preferred embodiment, compounds (I) wherein the bond between $C_7$ and $C_8$ is a double bond, which are compounds of formula (I-a), as defined above, may be prepared by as outlined in the following reaction scheme:

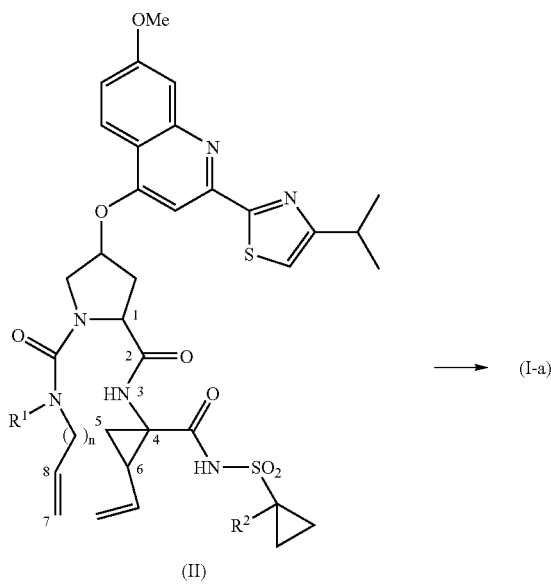

(II) → (I-a)

Formation of the macrocycle can be carried out via an olefin metathesis reaction in the presence of a suitable metal catalyst such as e.g. the Ru-based catalyst reported by Miller, S. J., Blackwell, H. E., Grubbs, R. H. J. Am. Chem. Soc. 118, (1996), 9606-9614; Kingsbury, J. S., Harrity, J. P. A., Bonitatebus, P. J., Hoveyda, A. H., J. Am. Chem. Soc. 121, (1999), 791-799; and Huang et al., J. Am. Chem. Soc. 121, (1999), 2674-2678; for example a Hoveyda-Grubbs catalyst.

Air-stable ruthenium catalysts such as bis(tricyclohexylphosphine)-3-phenyl-1H-inden-1-ylidene ruthenium chloride (Neolyst M1®) or bis(tricyclohexylphosphine)-[(phenylthio)methylene]ruthenium (IV) dichloride can be used. Other catalysts that can be used are Grubbs first and second generation catalysts, i.e. Benzylidene-bis(tricyclohexylphosphine)dichlororuthenium and (1,3-bis-(2,4,6-trimethylphenyl)-2-imidazolidinylidene)dichloro(phenylmethylene)-(tricyclohexylphosphine)ruthenium, respectively. Of particular interest are the Hoveyda-Grubbs first and second generation catalysts, which are dichloro(o-isopropoxyphenylmethylene)(tricyclohexylphosphine)-ruthenium(II) and 1,3-bis-(2, 4,6-trimethylphenyl)-2-imidazolidinylidene)dichloro(o-isopropoxyphenylmethylene)ruthenium respectively. Also other catalysts containing other transition metals such as Mo can be used for this reaction.

The metathesis reactions may be conducted in a suitable solvent such as for example ethers, e.g. THF, dioxane; halogenated hydrocarbons, e.g. dichoromethane, $CHCl_3$, 1,2-dichloroethane and the like. In a preferred embodiment, the metathesis reaction is conducted in toluene. These reactions are conducted at increased temperatures under nitrogen atmosphere.

Compounds of formula (I) wherein the link between C7 and C8 in the macrocycle is a single bond, i.e. compounds of formula (I-b), can be prepared from the compounds of formula (I-a) by a reduction of the C7-C8 double bond in the compounds of formula (I-a). This reduction may be conducted by catalytic hydrogenation with hydrogen in the presence of a noble metal catalyst such as, for example, Pt, Pd, Rh, Ru or Raney nickel. Of interest is Rh on alumina. The hydrogenation reaction preferably is conducted in a solvent such as, e.g. an alcohol such as methanol, ethanol, or an ether such as THF, or mixtures thereof. Water can also be added to these solvents or solvent mixtures.

The tail P1' can be connected to the P1 building block at any stage of the synthesis, i.e. before or after the cyclization, or before or after the cyclization and reduction as explained herein above. P1' can be linked to P1 by forming an amide bond between both moieties. In one embodiment, the P1' group is introduced in the last step of the synthesis of the compounds (I) as outlined in the following reaction scheme wherein G represents a group:

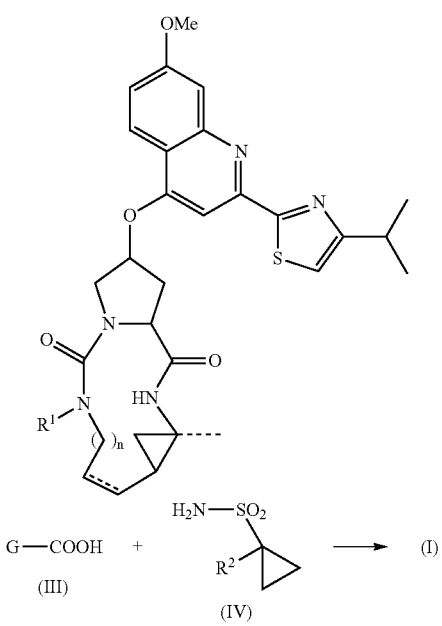

(III) G—COOH + (IV) H$_2$N—SO$_2$—R$^2$ ⟶ (I)

In this procedure, a cyclopropylsulfonamide (IV) is reacted with an intermediate (III) via an amide forming reaction such as any of the procedures for the formation of an amide bond described hereinafter. In particular, (III) may be treated with a coupling agent, for example N,N'-carbonyldiimidazole (CDI), EEDQ, IIDQ, EDCI or benzotriazol-1-yl-oxy-tris-pyrrolidinophosphonium hexafluorophosphate (commercially available as PyBOP®), in a solvent like THF, followed by reaction with the desired cyclopropylsulfonamide (IV) in the presence of a base for example a trialkylamine such as triethylamine or diisopropylethylamine, or 1,8-diazabicyclo-[5.4.0]undec-7-ene (DBU) or diisopropylethylamine.

The activation of the carboxylic acid in (III) as described in the above reactions may lead to an internal cyclization reaction to an azalactone intermediate of formula

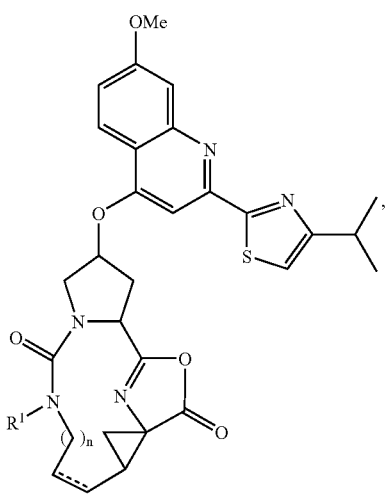

(III-a)

wherein R$^1$ and n are as specified above and wherein the stereogenic centers may have the stereochemical configuration as specified above, in particular as in (I-c). The intermediates (III-a) can be isolated from the reaction mixture, using conventional methodology, and the isolated intermediate (III-a) is then reacted with (IV), or the reaction mixture containing (III-a) can be reacted further with (IV) without isolation of (III-a). In one embodiment, where the reaction with the coupling agent is conducted in a water-immiscible solvent, the reaction mixture containing (III-a) may be washed with water or with slightly basic water in order to remove all water-soluble side products. The thus obtained washed solution may then be reacted with (IV) without additional purification steps. The isolation of intermediates (III-a) on the other hand may provide certain advantages in that the isolated product, after optional further purification, may be reacted with (IV), giving rise to less side products and an easier work-up of the reaction.

The compounds of formula (I) can also be prepared by etherifying an intermediate (V) with a quinoline of formula (VI) as outlined in the following reaction scheme:

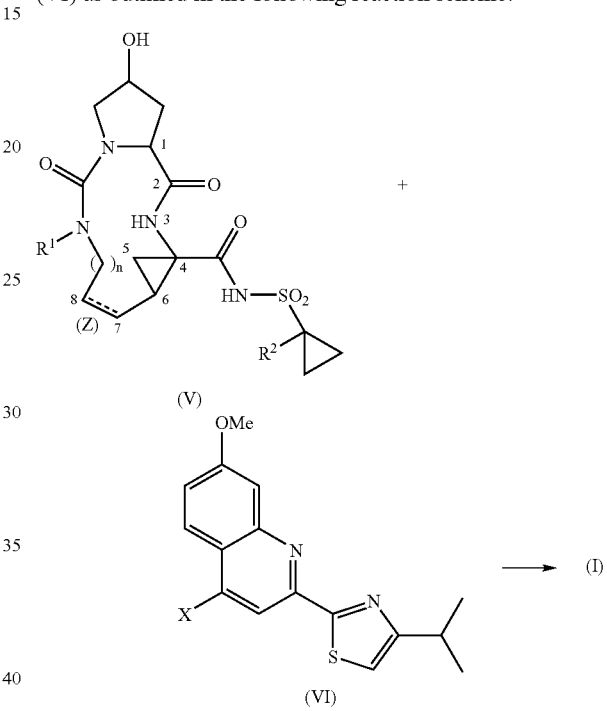

X in (VI) represents hydroxy or a leaving group such as a halide, e.g. bromide or chloride, or an arylsulfonyl group, e.g. mesylate, triflate or tosylate and the like.

In one embodiment, the reaction of (V) with (VI) is an O-arylation reaction and X represents a leaving group. This reaction can be conducted following the procedures described by E. M. Smith et al. (J. Med. Chem. (1988), 31, 875-885). In particular, this reaction is conducted in the presence of a base, preferably a strong base, in a reaction-inert solvent, e.g. one of the solvents mentioned for the formation of an amide bond.

In one embodiment, starting material (V) is reacted with quinoline (VI) in the presence of a base which is strong enough to detract a hydrogen from the hydroxy group, for example an alkali of alkaline metal hydride such as LiH or sodium hydride, or alkali metal alkoxide such as sodium or potassium methoxide or ethoxide, potassium tert-butoxide, in a reaction inert solvent like a dipolar aprotic solvent, e.g. DMA, DMF and the like. The resulting alcoholate is reacted with the arylating agent (VII), wherein X is a suitable leaving group as mentioned above. The conversion of (V) to (I) using an O-arylation reaction does not change the stereochemical configuration at the carbon bearing the hydroxy or —O-quinoline group.

Alternatively, the reaction of (V) with (VI) can also be conducted via a Mitsunobu reaction (Mitsunobu, 1981, Synthesis, January, 1-28; Rano et al., Tetrahedron Lett., 1995, 36, 22, 3779-3792; Krchnak et al., Tetrahedron Lett., 1995, 36, 5, 6193-6196; Richter et al., Tetrahedron Lett., 1994, 35, 27, 4705-4706). This reaction comprises treatment of intermediate (V) with quinoline (VI) wherein X is hydroxyl, in the presence of triphenylphosphine and an activating agent such as a dialkyl azocarboxylate, e.g. diethyl azodicarboxylate (DEAD), diisopropyl azodicarboxylate (DIAD) or the like. The Mitsunobu reaction changes the stereochemical configuration at the carbon bearing the hydroxy or —O-quinoline group.

The compounds of formula (I) wherein $R^1$ is hydrogen, said compounds being represented by (I-d) can also be prepared from a corresponding nitrogen-protected intermediate (VII) wherein PG represents a nitrogen protecting group. Suitable N-protecting groups are described hereinafter. In one embodiment, PG in (VII) is benzyl or substituted benzyl, in particular 4-methoxybenzyl.

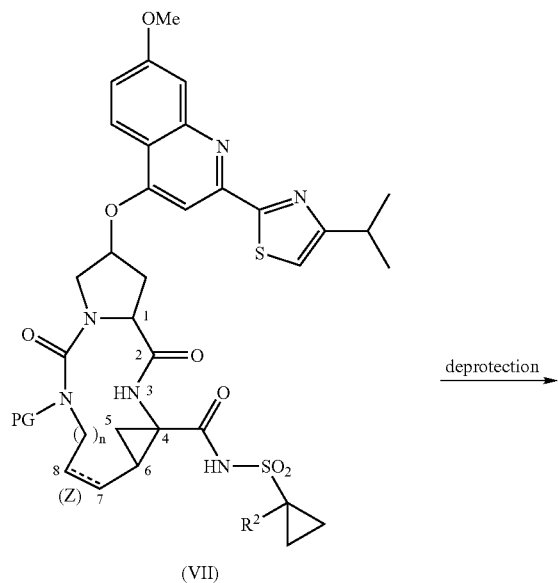

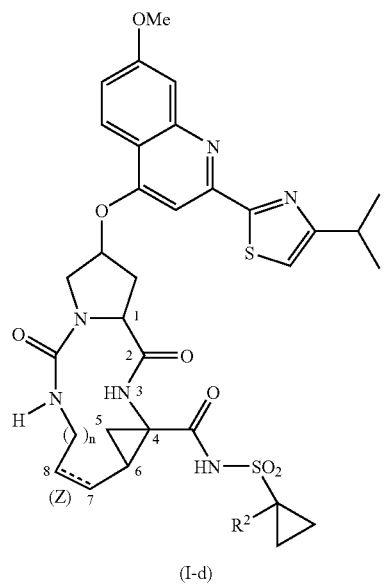

The starting materials (VII) in the above reaction can be prepared following the procedures described for the preparation of the compounds of formula (I), but using intermediates wherein the group $R^1$ is PG.

Alternatively, in order to prepare the compounds of formula (I), first an amide bond between building blocks P2 and P1 is formed, followed by coupling of the P3 building block to the P1 moiety in P1-P2, and a subsequent amide bond formation between P3 and the P2 moiety in P2-P1-P3 with concomitant ring closure. Yet again, the tail P1' can be bonded to the P1 building block at any stage of the synthesis of the compounds of formula (I), for example before or after coupling the building blocks P2 and P1; before or after coupling the P3 building block to P1; or before or after coupling building blocks P3 and P2 and the concomitant ring closure.

Yet another alternative synthetic methodology is the formation of an amide bond between building blocks P2 and P3, followed by the coupling of building block P1 to P3, and a last amide bond formation between P1 and P2 with concomitant ring closure. Yet again, the tail P1' can be bonded to the P1 building block at any stage of the synthesis of the compounds of formula (I), i.e. in the present case, before or after coupling the building blocks P2 and P3; before or after coupling the building blocks P1 and P3; before or after coupling P1 and P2 with concomitant ring closure.

Building blocks P1 and P3 can be linked via double bond formation at carbons 7 and 8, if desired, followed by a reduction of the C7-C8 double bond. The thus formed P1-P3 block can be coupled to building block P2 and subsequently cyclized, by forming amide bonds. In a preferred embodiment, building block P1-P3 is not reduced and coupled as such with P2 and cyclized, yielding compounds (I-1).

Building blocks P1 and P3 in any of the previous approaches can be linked via double bond formation, e.g. by the olefin metathesis reaction described hereinafter, or a Wittig type reaction.

It should be noted that in compounds of formula (I), the amide bond formation between blocks P2 and P3 may be accomplished at two different positions of the urea moiety. A first amide bond formation encompasses reacting the nitrogen of the pyrrolidine ring with the adjacent activated carbonyl (marked with an asterisk) being part of the P3 building block. An alternative second amide bond formation involves the reaction of the asterisked activated carbonyl being part of the P2 building block with an $NHRR^1$ group, wherein $R^1$ is as defined for the compounds of formula (I) or a subgroup thereof, and wherein $R^1$ may further be a nitrogen-protecting group; and R is the P3 alkyl moiety. The activated asterisked carbonyl can be introduced by reacting the pyrrolidine or amine $NHRR^1$ with phosgene or a phosgene derivative.

The individual building blocks can first be prepared and subsequently coupled together or alternatively, precursors of the building blocks can be coupled together and modified at a later stage to the desired molecular composition.

The functionalities in each of the building blocks may be protected to avoid side reactions.

The formation of amide bonds can be carried out using standard procedures such as those used for coupling amino acids in peptide synthesis. The latter involves the dehydrative coupling of a carboxyl group of one reactant with an amino group of the other reactant to form a linking amide bond. The amide bond formation may be performed by reacting the starting materials in the presence of a coupling agent or by converting the carboxyl functionality into an active form such as an active ester, mixed anhydride or a carboxyl acid chloride or bromide. General descriptions of such coupling reactions and the reagents used therein can be found in general textbooks on peptide chemistry, for example, M. Bodanszky, "Peptide Chemistry", 2nd rev. ed., Springer-Verlag, Berlin, Germany, (1993).

Examples of coupling reactions with amide bond formation include the azide method, mixed carbonic-carboxylic acid anhydride (isobutyl chloroformate) method, the carbodiimide(dicyclohexylcarbodiimide, diisopropylcarbodiimide, or water-soluble carbodiimide such as N-ethyl-N'-[(3-dimethylamino)propyl]carbodiimide) method, the active ester (p-nitrophenyl ester, N-hydroxysuccinic imido ester) method, the Woodward reagent K-method, the 1,1-carbonyldiimidazole (CDI or N,N'-carbonyldiimidazole) method, the phosphorus reagents or oxidation-reduction methods. Some of these methods can be enhanced by adding suitable catalysts, e.g. in the carbodiimide method by adding 1-hydroxybenzotriazole, DBU (1,8-diazabicyclo-[5.4.0]undec-7-ene), or 4-DMAP. Further coupling agents are (benzotriazol-1-yloxy)-tris-(dimethylamino) phosphonium hexafluorophosphate, either by itself or in the presence of 1-hydroxybenzotriazole or 4-DMAP; or 2-(1H-benzotriazol-1-yl)-N,N,N',N'-tetra-methyluronium tetrafluoroborate, or O—(7-azabenzotriazol-1-yl)-N,N,N',N'-tetramethyluronium hexafluorophosphate. These coupling reactions can be performed in either solution (liquid phase) or solid phase.

A preferred amide bond formation is performed employing N-ethyloxycarbonyl-2-ethyloxy-1,2-dihydroquinoline (EEDQ) or N-isobutyloxy-carbonyl-2-isobutyloxy-1,2-dihydroquinoline (IIDQ). Unlike the classical anhydride procedure, EEDQ and IIDQ do not require base nor low reaction temperatures. Typically, the procedure involves reacting equimolar amounts of the carboxyl and amine components in an organic solvent (a wide variety of solvents can be used). Then EEDQ or IIDQ is added in excess and the mixture is allowed to stir at room temperature.

The coupling reactions preferably are conducted in an inert solvent, such as halogenated hydrocarbons, e.g. dichloromethane, chloroform, dipolar aprotic solvents such as acetonitrile, dimethylformamide, dimethylacetamide, DMSO, HMPT, ethers such as tetrahydrofuran (THF).

In many instances the coupling reactions are done in the presence of a suitable base such as a tertiary amine, e.g. triethylamine, diisopropylethylamine (DIPEA), N-methylmorpholine, N-methylpyrrolidine, 4-DMAP or 1,8-diazabicycle[5.4.0]undec-7-ene (DBU). The reaction temperature may range between 0° C. and 50° C. and the reaction time may range between 15 min and 24 h.

The functional groups in the building blocks that are linked together may be protected to avoid formation of undesired bonds. Appropriate protecting groups that can be used are listed for example in Greene, "Protective Groups in Organic Chemistry", John Wiley & Sons, New York (1999) and "The Peptides: Analysis, Synthesis, Biology", Vol. 9, Academic Press, New York (1987), hereafter referred to simply as Greene.

Carboxyl groups can be protected as an ester that can be cleaved off to give the carboxylic acid. Protecting groups that can be used include 1) alkyl esters such as methyl, trimethylsilyl and tert-butyl; 2) arylalkyl esters such as benzyl and substituted benzyl; or 3) esters that can be cleaved by a mild base or mild reductive means such as trichloroethyl and phenacyl esters.

Amino groups can be protected by a variety of N-protecting groups, such as:

1) acyl groups such as formyl, trifluoroacetyl, phthalyl, and p-toluenesulfonyl;
2) aromatic carbamate groups such as benzyloxycarbonyl (Cbz or Z) and substituted benzyloxycarbonyls, and 9-fluorenylmethyloxycarbonyl (Fmoc);
3) aliphatic carbamate groups such as tert-butyloxycarbonyl (Boc), ethoxycarbonyl, diisopropylmethoxy-carbonyl, and allyloxycarbonyl;
4) cyclic alkyl carbamate groups such as cyclopentyloxycarbonyl and adamantyloxycarbonyl;
5) alkyl groups such as triphenylmethyl, benzyl or substituted benzyl such as 4-methoxybenzyl;
6) trialkylsilyl such as trimethylsilyl or t.Bu dimethylsilyl; and
7) thiol containing groups such as phenylthiocarbonyl and dithiasuccinoyl. Interesting amino protecting groups are Boc and Fmoc.

Preferably the amino protecting group is cleaved off prior to the next coupling step. Removal of N-protecting groups can be done following art-known procedures. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethyl-formamide. When the Fmoc group is used, the reagents of choice are piperidine or substituted piperidine in dimethylformamide, but any secondary amine can be used. The deprotection is carried out at a temperature between 0° C. and room temperature, usually around 15-25° C., or 20-22° C.

Other functional groups that can interfere in the coupling reactions of the building blocks may also be protected. For example hydroxyl groups may be protected as benzyl or substituted benzyl ethers, e.g. 4-methoxybenzyl ether, benzoyl or substituted benzoyl esters, e.g. 4-nitrobenzoyl ester, or with trialkylsilyl goups (e.g. trimethylsilyl or tert-butyldimethylsilyl).

Further amino groups may be protected by protecting groups that can be cleaved off selectively. For example, when Boc is used as the α-amino protecting group, the following side chain protecting groups are suitable: p-toluenesulfonyl (tosyl) moieties can be used to protect further amino groups; benzyl (Bn) ethers can be used to protect hydroxy groups; and benzyl esters can be used to protect further carboxyl groups. Or when Fmoc is chosen for the α-amino protection, usually tert-butyl based protecting groups are acceptable. For instance, Boc can be used for further amino groups; tert-butyl ethers for hydroxyl groups; and tert-butyl esters for further carboxyl groups.

Any of the protecting groups may be removed at any stage of the synthesis procedure but preferably, the protecting groups of any of the functionalities not involved in the reaction steps are removed after completion of the build-up of the macrocycle. Removal of the protecting groups can be done in whatever manner is dictated by the choice of protecting groups, which manners are well known to those skilled in the art.

The intermediates of formula (II) may be prepared by reacting an intermediate (VIII) with an alkenamine (IX) in the presence of a carbonyl introducing agent as outlined in the following reaction scheme.

19

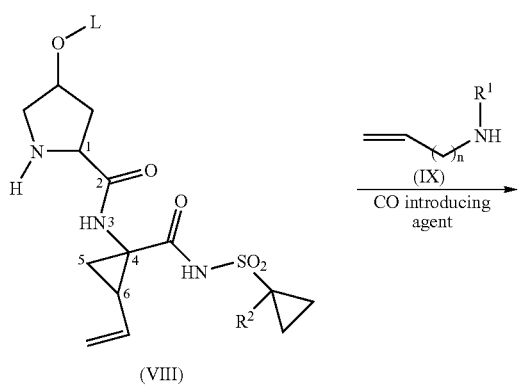

(VIII)

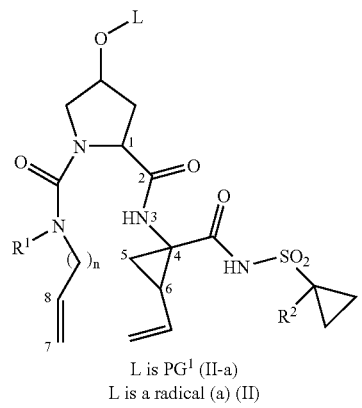

L is PG¹ (II-a)
L is a radical (a) (II)

L represents an O-protecting group PG¹ or a group

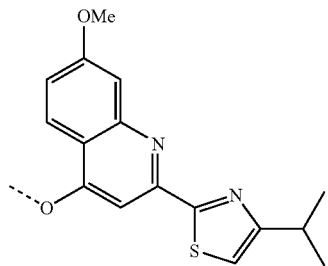

(a)

The O-protecting group can be any of the groups mentioned herein and in particular is a benzoyl or substituted benzoyl group such as 4-nitrobenzoyl.

Carbonyl (CO) introducing agents include phosgene, or phosgene derivatives such as carbonyl diimidazole (CDI), and the like. In one embodiment (VIII) is reacted with the CO introducing agent in the presence of a suitable base and a solvent, which can be the bases and solvents used in the amide forming reactions as described above. In a particular embodiment, the base is a hydrogencarbonate, e.g. NaHCO$_3$ or a tertiary amine such as triethylamine and the like, and the solvent is an ether or halogenated hydrocarbon, e.g. THF, CH$_2$Cl$_2$, CHCl$_3$, and the like. Thereafter, the amine (IX) is added thereby obtaining intermediates (XII) or (XII-a) as in the above scheme. An alternative route using similar reaction conditions involves first reacting the CO introducing agent with the amine (IX) and then reacting the thus formed intermediate with (VIII).

Where L is PG¹ the reaction of (VIII) with (IX) yields intermediates (II-a). These can be deprotected, for example

20 where PG¹ is benzoyl or substituted benzoyl by reaction with a an alkali metal hydroxide (LiOH, NaOH, KOH), in particular where PG¹ is 4-nitrobenzoyl, with LiOH, in an aqueous medium comprising water and a water-soluble organic solvent such as an alkanol (methanol, ethanol) and THF. The resulting alcohol (i.e. an intermediate (II-a) wherein L is hydrogen), is reacted with an intermediate (VI) as described above for the reaction of (V) with (VI) and this reaction results in intermediates (II).

The intermediates of formula (III) may be prepared by first cyclizing an ester intermediate (X) to a macrocyclic ester (XI), which in turn is converted to the corresponding macrocyclic carboxylic acid (III) as follows:

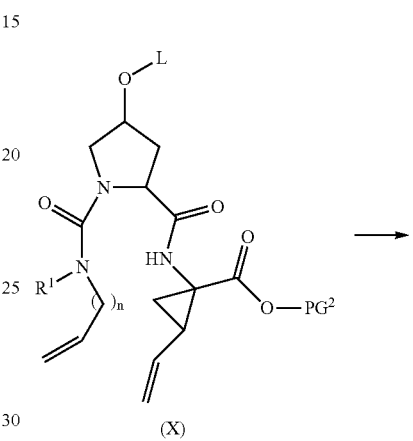

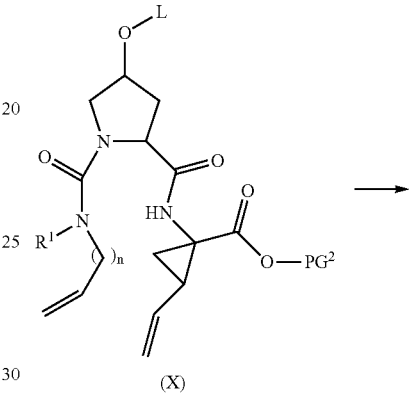

L is PG¹ (III-a)
L is a radical (a) (III)

L is as specified above and PG² is a carboxyl protecting group, e.g. one of the carboxyl protecting groups mentioned above, in particular a C$_{1-4}$alkyl or benzyl ester, e.g. a methyl, ethyl or t.butyl ester. The PG¹ group mat be removed using art-known methodologies, e.g. methyl or ethyl esters by treatment with an alkali metal hydroxide in an aqueous medium, t.butyl esters with weak acid and benzyl esters with strong acid or by catalytic hydrogenation. Where L is a radical (a) this reaction sequence yields intermediates (III). These can also prepared by removing L being an O-protecting group and etherifying the thus formed alcohol with intermediate (VI) as described above.

The intermediates of formula (VII) may be prepared by cyclizing an intermediate (XII) wherein PG is a nitrogen-protecting group as specified above to intermediates (VII) with a double bond in the macrocycle (VII-a), which can be reduced to the corresponding intermediates (VII) with a single bond at that location in the macrocycle (VII-b):

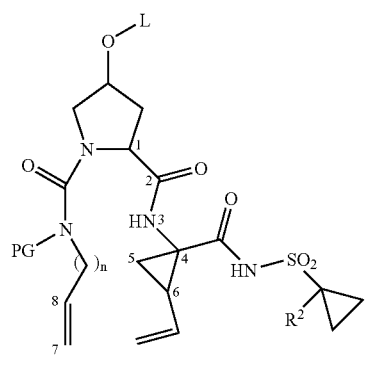

(XII)

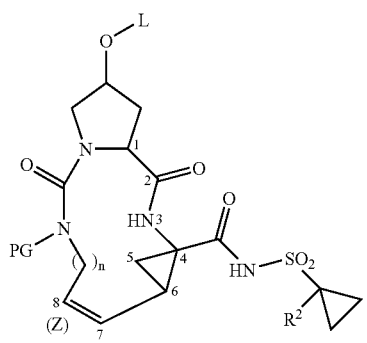

L is PG¹ (VII-a-1)
L is radical (a) (VII-a)

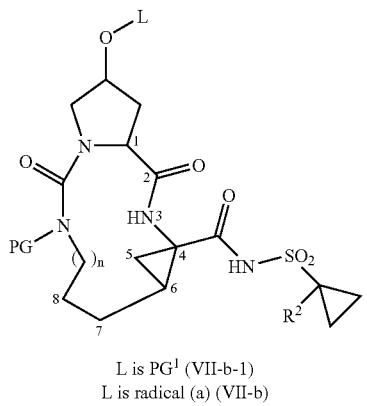

L is PG¹ (VII-b-1)
L is radical (a) (VII-b)

L is as specified above. Where L is a radical (a) this reaction sequence yields intermediates (VII-a) or (VII-b). These can also prepared by removing L being an O-protecting group and etherifying the thus formed alcohol with intermediate (VI) as described above. The sulfonylamide group in the above sequence may be an ester (i.e. an —OPG² group as specified above) which may be removed and condensed with a cyclopropylamide (IV) following the procedures mentioned earlier.

The cyclopropylsulfonamide group can be introduced at any stage of the synthesis, either as the last step as described above, or earlier, before the macrocycle formation as shown in the following scheme.

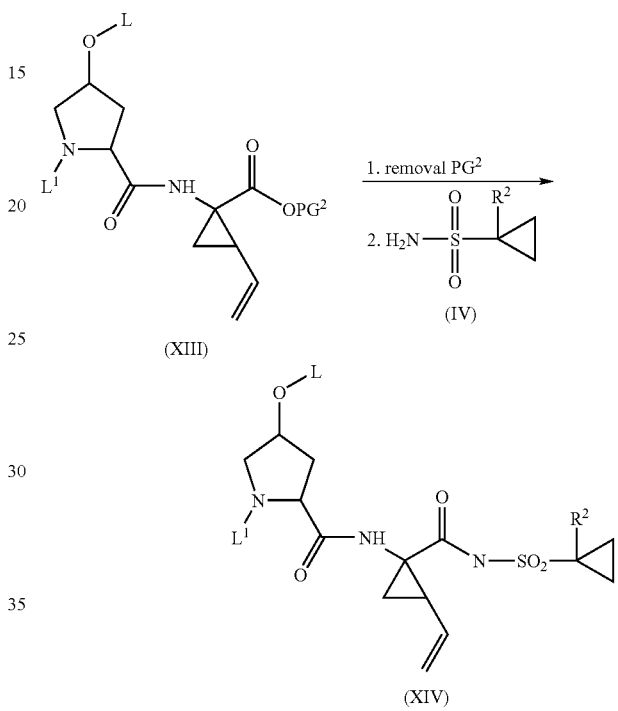

L is as defined above, PG² represents a carboxyl protecting group, as specified above, and L¹ is a nitrogen-protecting group (PG, as defined above), or L¹ is a group

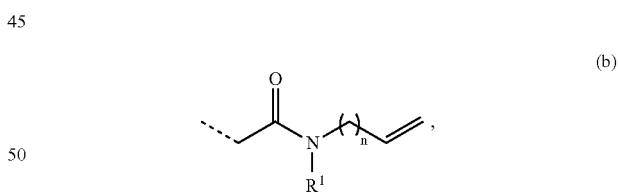

(b)

wherein R¹ and n are as defined above, or wherein R¹ may also represent a nitrogen-protecting group (a group PG, as specified above). Obviously, when R¹ represents a nitrogen-protecting group, such may be removed at the desired stage of the synthetic route. The intermediates (XIV) wherein L¹ represents a group (b) correspond to the intermediates (II) or (II-a) and may be processed further as specified above.

Coupling of P1 and P2 Building Blocks

The P1 and P2 building blocks are linked using an amide forming reaction following the procedures described above. The P1 building block may have a carboxyl protecting group PG2 (as in (XVI-a)) or may already be linked to P1' group (as in (XVI-b)). L² is hydrogen or a group L as specified above.

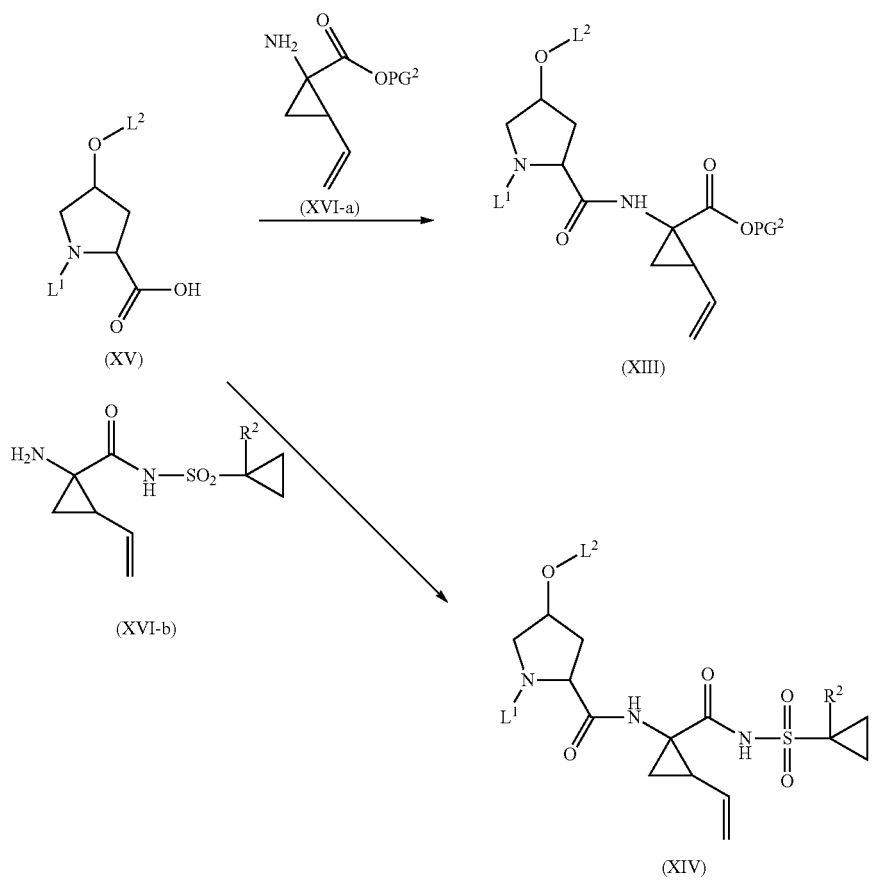

In the procedure of the above scheme, a cyclopropyl amino acid (XVI-a) or (XVI-b) is coupled to the acid function of the P2 building block using an amide forming reaction such as the standard peptide coupling conditions described above. Removal of the acid protection group in (XIII), using the appropriate conditions for the protecting group used, followed by coupling with a cyclopropylsulfonamide (IV) as described above, again yields intermediate (XIV).

In one embodiment, $L^1$ is a group (b) and these reactions involve coupling P1 to P2-P3, which results in the intermediates (X) or (II) mentioned above. In another embodiment, $L^1$ is a N-protecting group PG, which is as specified above, and the coupling reaction results in an intermediate (XV-a) from which the group PG can be removed to intermediates (XIII-a), using reaction conditions also mentioned above:

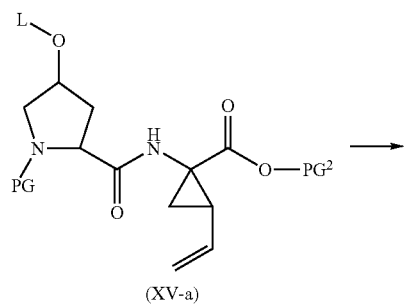

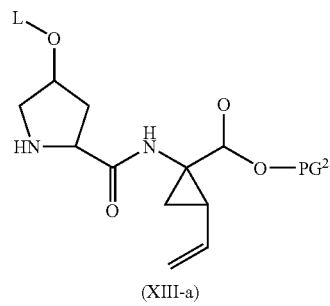

In one embodiment, PG in this reaction is a BOC group. Where additionally $L^3$ is hydrogen, the starting material is Boc-L-hydroxyproline.

The group $L^2$ can be an O-protecting group $PG^1$ which is introduced on the starting material (XV), wherein $L^2$ is hydrogen and which is selectively cleavable towards group PG.

Coupling of P3 and P2 Building Blocks

The P3 and P2 building blocks are linked using a urea forming reaction following the procedures described above for the coupling of (VII) with (IX). A general procedure is represented in the following reaction scheme wherein L is as specified above and $L^3$ is a group —O—$PG^2$, or a group

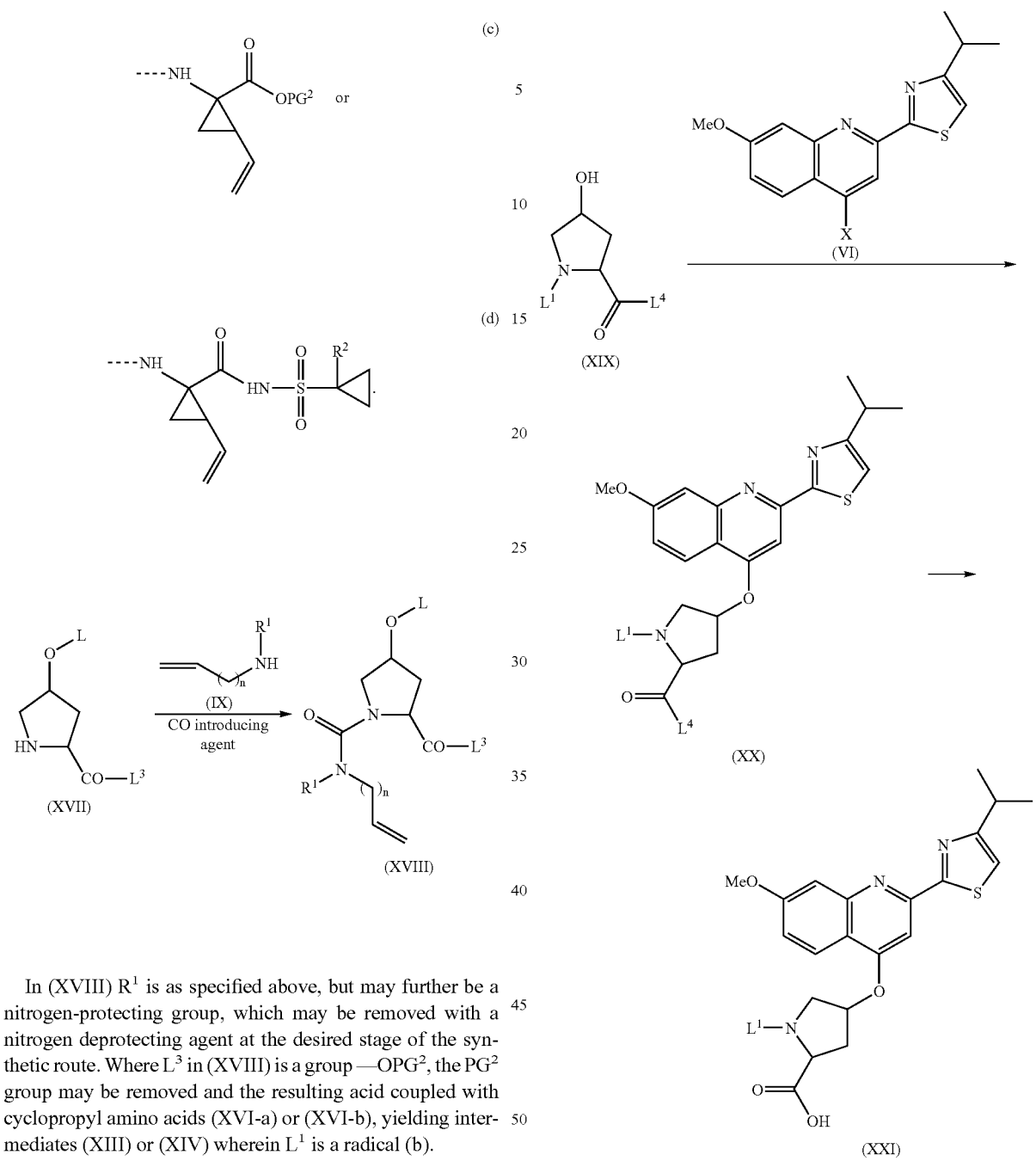

In (XVIII) R[1] is as specified above, but may further be a nitrogen-protecting group, which may be removed with a nitrogen deprotecting agent at the desired stage of the synthetic route. Where L[3] in (XVIII) is a group —OPG[2], the PG[2] group may be removed and the resulting acid coupled with cyclopropyl amino acids (XVI-a) or (XVI-b), yielding intermediates (XIII) or (XIV) wherein L[1] is a radical (b).

The building blocks P1, P1', P2 and P3 for compounds of formula (I) can be prepared starting from art-known intermediates. A number of such syntheses are described hereafter in more detail.

Synthesis of P2 Building Blocks

Building blocks P2 can be prepared by an O-arylation reaction, e.g. following the procedures described above, as depicted in the scheme below, wherein L[1] is as specified above and in particular is a N-protecting group PG, X is as defined above and L[4] is hydroxy, a group —OPG[2], with PG[2] being a carboxyl protecting group, such as any of the carboxyl protecting groups mentioned above; or L[4] is a P1 group such as a group (c) or (d) as defined above.

Starting material (XIX) is reacted with reagent (VI) as described above for the synthesis of (I-d) starting from (V) and (VI). Similarly as described above, this reaction can be done with retention (arylation with X being a leaving group) or inversion (Mitsunobu reaction) of the stereochemistry at the hydroxy bearing carbon atom. In the arylation with X being a leaving group, L[4] may also be hydroxy, in the Mitsunobu reaction L[4] is a group —OPG[2].

In one embodiment the group L[1] is PG, which is Boc and the starting material (VIII) is commercially available Boc-L-hydroxyproline, or any other stereoisomeric form thereof.

Where L[4] in (XX) is —OPG[2], the carboxyl protecting group PG[2] may be removed following procedures described above to hydroxyproline derivatives (XVII). In one embodiment PG¹ is Boc and PG² is a lower alkyl ester, in particular a methyl or ethyl ester. Hydrolysis of the latter ester to the acid can be done by standard procedures, e.g. acid hydrolysis with hydrochloric acid in methanol or ethanol, or by a metal hydroxide such as sodium or preferably lithium hydroxide.

The intermediates (VI) can be prepared following art-known methods using known starting materials. They may be prepared as shown below:

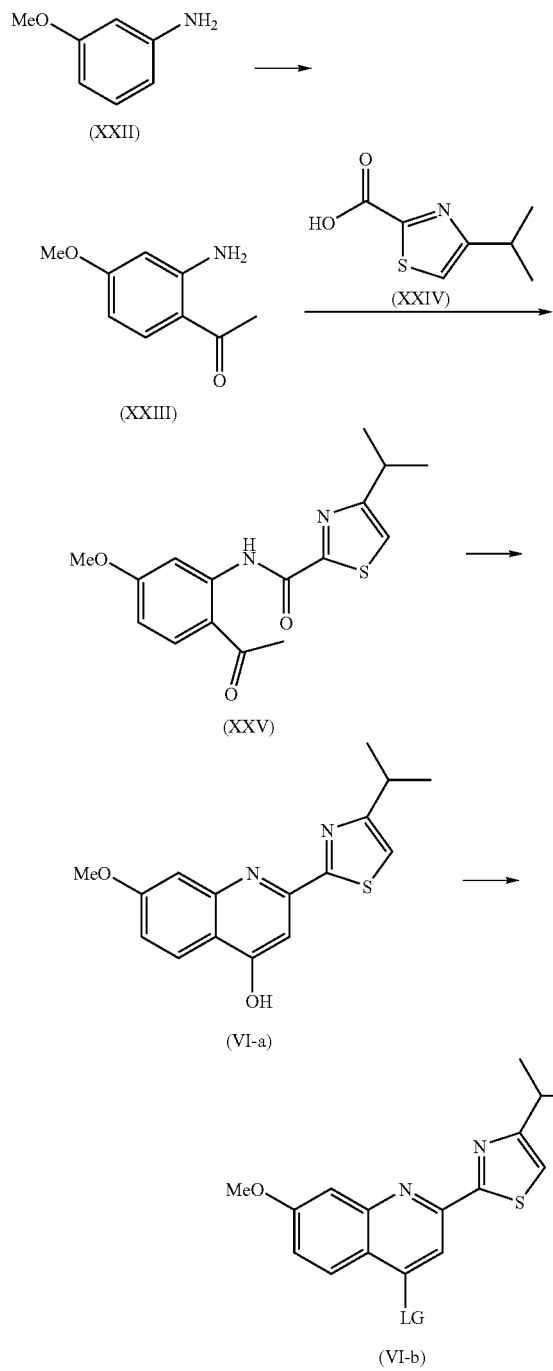

Friedel-Craft acylation of a 3-methoxyaniline (XXII), available either commercially or via art-known procedures, using an acylating agent such as acetyl chloride or the like in the presence of one or more Lewis acids such as boron trichloride and aluminium trichloride in a solvent like dichloromethane provides (XXIII). Coupling of (XXIII) with 4-isopropyl-thiazole-2-carboxylic acid (XXIV), preferably under basic conditions, such as in pyridine, in the presence of an activating agent for the carboxylate group, for instance POCl₃, followed by ring closure and dehydration under basic conditions like potassium tert-butoxide in tert-butanol yields quinoline derivative (VI-a). The latter can be converted to (VI-b) wherein LG is a leaving group, e.g. by reaction of (XII) with a halogenating agent, for example phosphoryl chloride or the like, or with an arylsulfonyl chloride, e.g. with tosyl chloride.

2-carboxy-4-isopropyl-thiazole (XXIV) is synthesized following art-known procedures, in particular as follows:

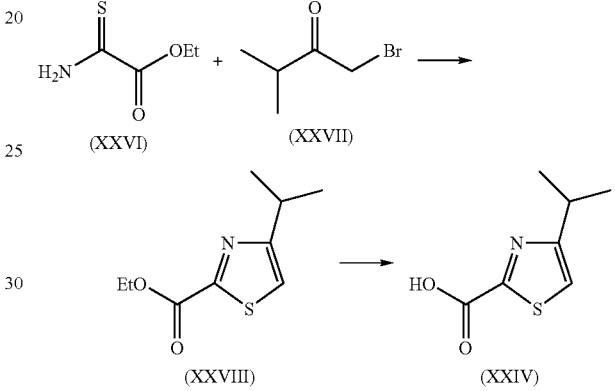

Ethyl thiooxamate (XXVI) is reacted with the β-bromoketone (XXVII) to form the thiazolyl carboxylic acid ester (XXVIII) which is hydrolyzed to the corresponding acid (XXIV). The ethyl ester in these intermediates may be replaced by other carboxyl protecting groups PG², as defined above.

Intermediate (XXII) may also be prepared as described by Brown et al. J. Med. Chem. 1989, 32, 807-826, or as outlined in the following scheme.

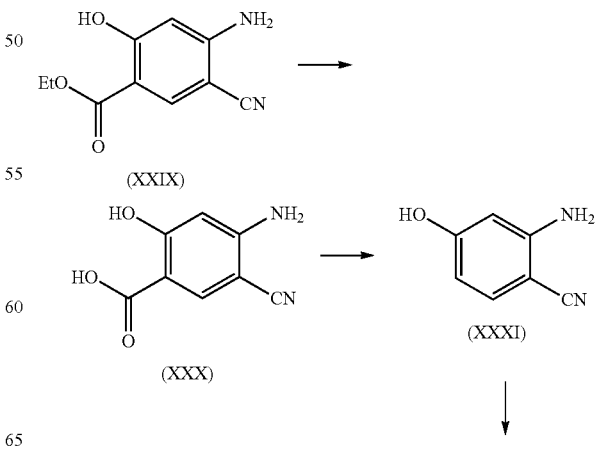

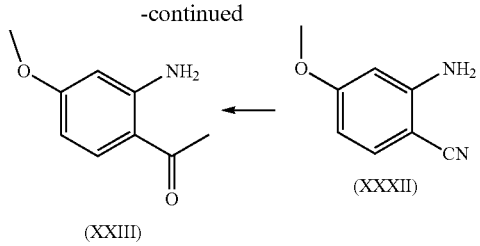

Starting materials ethylacetyl acetate and ethoxymethylene malononitrile, which are commercially available, are reacted in the presence of a suitable base, such as sodium ethoxide, and a solvent, such as ethanol and the like. This reaction affords intermediate (XXIX). The latter is hydrolyzed, e.g. with a base such as an alkali metal hydroxide, e.g. NaOH or LiOH, in a suitable solvent such as ethanol/water to produce (XXX). Decarboxylation of intermediate (XXX) into intermediate (XXXI) is performed at increased temperature until effervescence ceases, preferably in the presence of a basic solvent such as quinoline. Methylation of intermediate (XXXI), in particular with a methylating agent such as MeI in the presence of a suitable base (e.g. $K_2CO_3$) in a suitable solvent (such as DMF and the like) yields (XXXII). The latter is reacted with a Grignard reagent such as MeMgBr in the presence of a suitable solvent (e.g. THF), followed by hydrolysis, for instance with aqueous HCl, affording intermediate (XOH).

Synthesis of P1 Building Blocks

The cyclopropane amino acid used in the preparation of the P1 fragment is commercially available or can be prepared using art-known procedures.

The amino-vinyl-cyclopropyl ethyl ester (XVI-a) may be obtained according to the procedure described in WO 00/09543 or as illustrated in the following scheme, wherein $PG^2$ is a carboxyl protecting group as specified above:

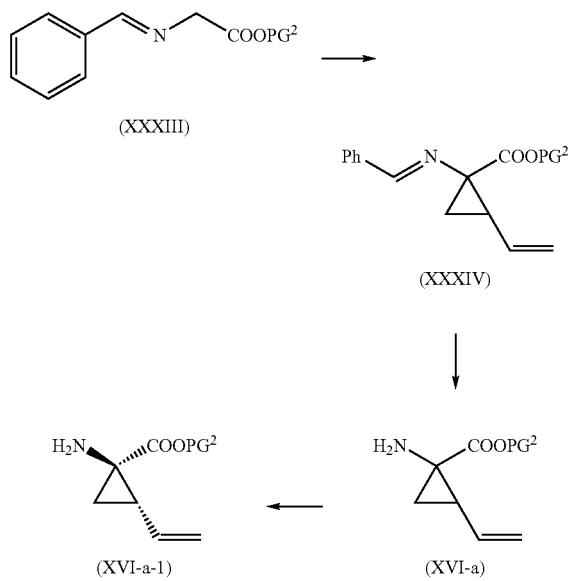

Treatment of commercially available or easily obtainable imine (XXXIII) with 1,4-dihalobutene in presence of a base produces (XXXIV), which after hydrolysis yields cyclopropyl amino acid (XVI-a), having the allyl substituent syn to the carboxyl group. Resolution of the enantiomeric mixture (XVI-a) results in (XVI-a-1). The resolution is performed using art-known procedures such as enzymatic separation; crystallization with a chiral acid; or chemical derivatization; or by chiral column chromatography.

The sulfonamide derivative (XVI-b) can be obtained as outlined in the following reaction scheme, wherein $R^2$ and PG are as specified above.

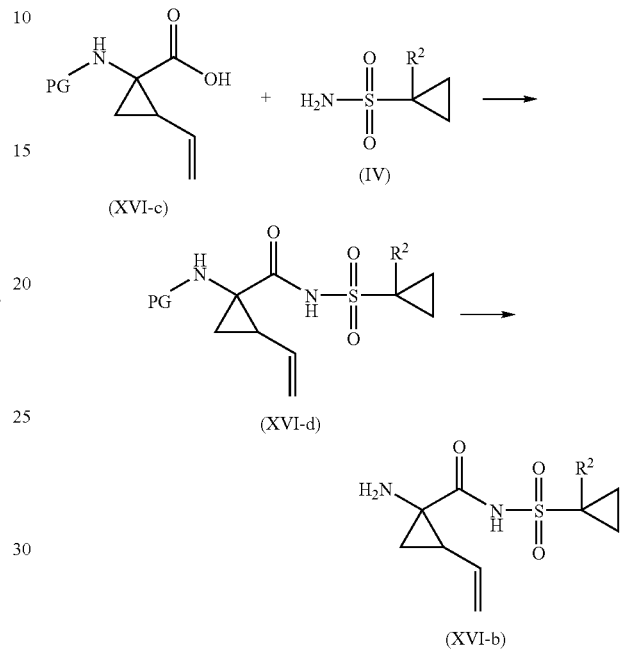

The reaction of (XVI-c) with sulfonamide (IV) is an amide forming procedure, which can be performed following the procedures described above. This reaction yields intermediates (XVI-d) from which the amino protecting group is removed by standard methods such as those described above. This in turn results in the desired intermediate (XVI-b). Starting materials (XVI-c) may be prepared from intermediates (XVI-a) by first introducing a N-protecting group PG and subsequent removal of the group $PG^2$.

Synthesis of the P3 Building Blocks

The P3 building blocks (IX) can be prepared according to methodologies known in the art. One of these methodologies is shown in the scheme below and starts from protected amines (XXXVI), in particular from monoacylated amines, such as trifluoroacetamide, or from a Boc-protected amine.

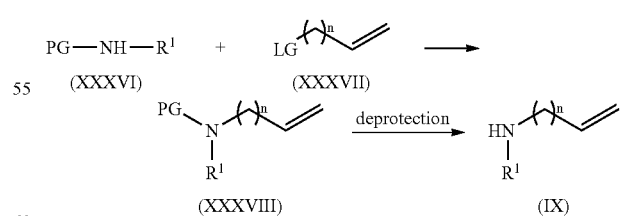

In this scheme, LG is a N-protecting group as specified above and in particular is BOC or trifluoroacetyl; $R^1$ and n are as defined above, and wherein $R^1$ may also be a further nitrogen-protecting group which can be cleaved off selectively towards the group PG. LG is a leaving group as specified above, in particular LG is chloro or bromo. Where $R^1$ represents a nitrogen-protecting group, it may be removed with a nitrogen deprotecting agent at the desired stage of the synthetic route.

The monoacylated amines (XXXVI) are treated with a strong base such as sodium hydride and are subsequently reacted with a haloC$_{3-8}$alkenyl (XXXVII) to the corresponding protected amine (XXXVIII). Deprotection of (XXXVIII) affords (IX). Deprotection will depend on the group PG, thus if PG is Boc, deprotection can be accomplished with a relatively weak acid, e.g. trifluoroacetic acid, or when PG is trifluoroacetyl, removal is accomplished with a base, e.g. sodium hydroxide.

Intermediates (IX) wherein $R^1$ is hydrogen can also be prepared via a Gabriel synthesis of an alkenylamine, which can be carried out by the treatment of a phthalimide (XXXIX) with a base, such as potassium hydroxide, and (XXXX), followed by the hydrolysis to generate an alkenylamine (IX-a).

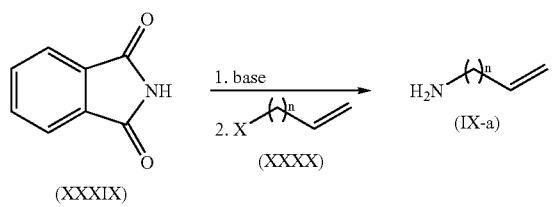

In the above scheme is LG halogen, n is as defined above.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) may be obtained as racemic mixtures of enantiomers which can be separated from one another following art-known resolution procedures. The racemic compounds of formula (I), which are sufficiently basic or acidic, may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereo-chemically isomeric forms may also be derived from the corresponding pure stereo-chemically isomeric forms of the appropriate starting materials, provided that the reaction occurs stereospecifically. Preferably if a specific stereoisomer is desired, said compound may be synthesized by stereospecific methods of preparation. These methods may advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylactically act against, to stabilize or to reduce viral infection, and in particular HCV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets.

Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. The compounds of the present invention may be administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections and their associated diseases treatable using the compounds and methods of the present invention include those infections brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and HCC; and for the other pathogenic flaviviruses the diseases include yellow fever, dengue fever, hemorrhagic fever and encephalitis. A number of the compounds of this invention moreover are active against mutated strains of HCV. Additionally, many of the compounds of this invention show a favorable pharmacokinetic profile and have attractive properties in terms of bioavailability, including an acceptable half-life, AUC (area under the curve) and peak values and lacking unfavorable phenomena such as insufficient quick onset and tissue retention.

The in vitro antiviral activity against HCV of the compounds of formula (I) was tested in a cellular HCV replicon system based on Lohmann et al. (1999) Science 285:110-113, with the further modifications described by Krieger et al. (2001), Journal of Virology 75: 4614-4624, which is further exemplified in the examples section. This model, while not a complete infection model for HCV, is widely accepted as the most robust and efficient model of autonomous HCV RNA replication currently available. Compounds exhibiting anti-HCV activity in this cellular model are considered as candidates for further development in the treatment of HCV infections in mammals. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula (I) or any subgroup thereof, their N-oxides, addition salts, quaternary amines, metal complexes and stereochemically isomeric forms, are useful in the treatment of individuals experiencing a viral infection, particularly a HCV infection, and for the prophylaxis of these infections. In general, the compounds of the present invention may be useful in the treatment of warm-blooded animals infected with viruses, in particular flaviviruses such as HCV.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the HCV infection.

The present invention also relates to the use of the present compounds or any subgroup thereof in the manufacture of a medicament for the treatment or the prevention of viral infections, particularly HCV infection.

The present invention furthermore relates to a method of treating a warm-blooded animal infected by a virus, or being at risk of infection by a virus, in particular by HCV, said method comprising the administration of an anti-virally effective amount of a compound of formula (I), as specified herein, or of a compound of any of the subgroups of compounds of formula (I), as specified herein.

Also, the combination of previously known anti-HCV compound, such as, for instance, interferon-α (IFN-α), pegylated interferon-α and/or ribavirin, and a compound of formula (I) can be used as a medicine in a combination therapy. The term "combination therapy" relates to a product containing mandatory (a) a compound of formula (I), and (b) optionally another anti-HCV compound, as a combined preparation for simultaneous, separate or sequential use in treatment of HCV infections, in particular, in the treatment of infections with HCV.

Anti-HCV compounds encompass agents selected from an HCV polymerase inhibitor, an HCV protease inhibitor, an inhibitor of another target in the HCV life cycle, and immunomodulatory agent, an antiviral agent, and combinations thereof.

HCV polymerase inhibitors include, but are not limited to, NM283 (valopicitabine), R803, JTK-109, JTK-003, HCV-371, HCV-086, HCV-796 and R-1479.

Inhibitors of HCV proteases (NS2-NS3 inhibitors and NS3-NS4A inhibitors) include, but are not limited to, the compounds of WO02/18369 (see, e.g., page 273, lines 9-22 and page 274, line 4 to page 276, line 11); BILN-2061, VX-950, GS-9132 (ACH-806), SCH-503034, and SCH-6. Further agents that can be used are those disclosed in WO98/17679, WO 00/056331 (Vertex); WO 98/22496 (Roche); WO 99/07734, (Boehringer Ingelheim), WO 2005/073216, WO 2005073195 (Medivir) and structurally similar agents.

Inhibitors of other targets in the HCV life cycle, including NS3 helicase; metallo-protease inhibitors; antisense oligonucleotide inhibitors, such as ISIS-14803, AVI-4065 and the like; siRNA's such as SIRPLEX-140-N and the like; vector-encoded short hairpin RNA (shRNA); DNAzymes; HCV specific ribozymes such as heptazyme, RPI.13919 and the like; entry inhibitors such as HepeX-C, HuMax-HepC and the like; alpha glucosidase inhibitors such as celgosivir, UT-231B and the like; KPE-02003002; and BIVN 401.

Immunomodulatory agents include, but are not limited to; natural and recombinant interferon isoform compounds, including α-interferon, β-interferon, γ-interferon, ω-interferon and the like, such as Intron A®, Roferon-A®, Canferon-A300®, Advaferon®, Infergen®, Humoferon®, Sumiferon MP®, Alfaferone®, IFN-beta®, Feron® and the like; polyethylene glycol derivatized (pegylated) interferon compounds, such as PEG interferon-α-2a (Pegasys®), PEG interferon-α-2b (PEG-Intron®), pegylated IFN-α-con1 and the like; long acting formulations and derivatizations of interferon compounds such as the albumin-fused interferon albuferon α and the like; compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isatoribine and the like; thymosin α-1; ANA-245; ANA-246; histamine dihydrochloride; propagermanium; tetrachlorodecaoxide; ampligen; IMP-321; KRN-7000; antibodies, such as civacir, XTL-6865 and the like; and prophylactic and therapeutic vaccines such as InnoVac C, HCV E1E2/MF59 and the like.

Other antiviral agents include, but are not limited to, ribavirin, amantadine, viramidine, nitazoxanide; telbivudine; NOV-205; taribavirin; inhibitors of internal ribosome entry; broad-spectrum viral inhibitors, such as IMPDH inhibitors (e.g., compounds of U.S. Pat. No. 5,807,876, U.S. Pat. No. 6,498,178, U.S. Pat. No. 6,344,465, U.S. Pat. No. 6,054,472, WO97/40028, WO98/40381, WO00/56331, and mycophenolic acid and derivatives thereof, and including, but not limited to VX-950, merimepodib (VX-497), VX-148, and/or VX-944); or combinations of any of the above.

Thus, to combat or treat HCV infections, the compounds of formula (I) may be co-administered in combination with for instance, interferon-α (IFN-α), pegylated interferon-α and/or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy preferably comprising a compound of formula (I) and another HCV inhibitory compound, e.g. (pegylated) IFN-α and/or ribavirin.

In still another aspect there are provided combinations of a compound of formula (I) as specified herein and an anti-HIV compound. The latter preferably are those HIV inhibitors that have a positive effect on drug metabolism and/or pharmacokinetics that improve bioavailabilty. An example of such an HIV inhibitor is ritonavir.

As such, the present invention further provides a combination comprising (a) an HCV NS3/4a protease inhibitor of formula (I) or a pharmaceutically acceptable salt thereof and (b) ritonavir or a pharmaceutically acceptable salt thereof.

The compound ritonavir, and pharmaceutically acceptable salts thereof, and methods for its preparation are described in WO94/14436. For preferred dosage forms of ritonavir, see U.S. Pat. No. 6,037,157, and the documents cited therein: U.S. Pat. No. 5,484,801, U.S. Ser. No. 08/402,690, and WO95/07696 and WO95/09614. Ritonavir has the following formula:

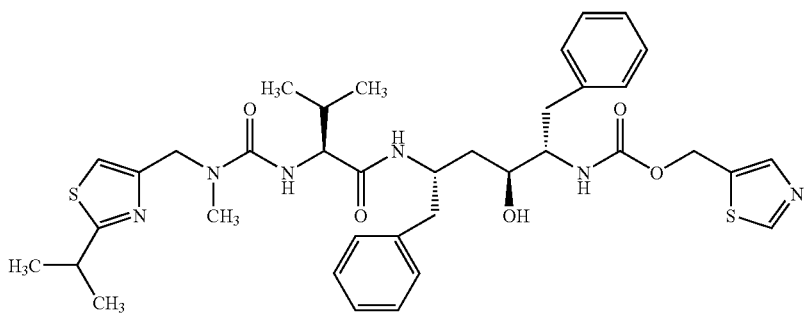

In a further embodiment, the combination comprising (a) an HCV NS3/4a protease inhibitor of formula (I) or a pharmaceutically acceptable salt thereof and (b) ritonavir or a pharmaceutically acceptable salt thereof; further comprises an additional anti-HCV compound selected from the compounds as described herein.

In one embodiment of the present invention there is provided a process for preparing a combination as described herein, comprising the step of combining an HCV NS3/4a protease inhibitor of formula (I) or a pharmaceutically acceptable salt thereof, and ritonavir or a pharmaceutically acceptable salt thereof. An alternative embodiment of this invention provides a process wherein the combination comprises one or more additional agent as described herein.

The combinations of the present invention may be used as medicaments. Said use as a medicine or method of treatment comprises the systemic administration to HCV-infected subjects of an amount effective to combat the conditions associated with HCV and other pathogenic flavi- and pestiviruses. Consequently, the combinations of the present invention can be used in the manufacture of a medicament useful for treating, preventing or combating infection or disease associated with HCV infection in a mammal, in particular for treating conditions associated with HCV and other pathogenic flavi- and pestiviruses.

In one embodiment of the present invention there is provided a pharmaceutical composition comprising a combination according to any one of the embodiments described herein and a pharmaceutically acceptable excipient. In particular, the present invention provides a pharmaceutical composition comprising (a) a therapeutically effective amount of an HCV NS3/4a protease inhibitor of the formula (I) or a pharmaceutically acceptable salt thereof, (b) a therapeutically effective amount of ritonavir or a pharmaceutically acceptable salt thereof, and (c) a pharmaceutically acceptable excipient. Optionally, the pharmaceutical composition further comprises an additional agent selected from an HCV polymerase inhibitor, an HCV protease inhibitor, an inhibitor of another target in the HCV life cycle, and immunomodulatory agent, an antiviral agent, and combinations thereof.

The compositions may be formulated into suitable pharmaceutical dosage forms such as the dosage forms described above. Each of the active ingredients may be formulated separately and the formulations may be co-administered or one formulation containing both and if desired further active ingredients may be provided.

As used herein, the term "composition" is intended to encompass a product comprising the specified ingredients, as well as any product which results, directly or indirectly, from the combination of the specified ingredients.

In one embodiment the combinations provided herein may also be formulated as a combined preparation for simultaneous, separate or sequential use in HIV therapy. In such a case, the compound of general formula (I) or any subgroup thereof, is formulated in a pharmaceutical composition containing other pharmaceutically acceptable excipients, and ritonavir is formulated separately in a pharmaceutical composition containing other pharmaceutically acceptable excipients. Conveniently, these two separate pharmaceutical compositions can be part of a kit for simultaneous, separate or sequential use.

Thus, the individual components of the combination of the present invention can be administered separately at different times during the course of therapy or concurrently in divided or single combination forms. The present invention is therefore to be understood as embracing all such regimes of simultaneous or alternating treatment and the term "administering" is to be interpreted accordingly. In a preferred embodiment, the separate dosage forms are administered about simultaneously.

In one embodiment, the combination of the present invention contains an amount of ritonavir, or a pharmaceutically acceptable salt thereof, which is sufficient to clinically improve the bioavailability of the HCV NS3/4a protease inhibitor of formula (I) relative to the bioavailability when said HCV NS3/4a protease inhibitor of formula (I) is administered alone.

In another embodiment, the combination of the present invention contains an amount of ritonavir, or a pharmaceutically acceptable salt thereof, which is sufficient to increase at least one of the pharmacokinetic variables of the HCV NS3/4a protease inhibitor of formula (I) selected from $t_{1/2}$, $C_{min}$, $C_{max}$, $C_{ss}$, AUC at 12 hours, or AUC at 24 hours, relative to said at least one pharmacokinetic variable when the HCV NS3/4a protease inhibitor of formula (I) is administered alone.

A further embodiment relates to a method for improving the bioavailability of a HCV NS3/4a protease inhibitor comprising administering to an individual in need of such improvement a combination as defined herein, comprising a therapeutically effective amount of each component of said combination.

In a further embodiment, the invention relates to the use of ritonavir or a pharmaceutically acceptable salt thereof, as an improver of at least one of the pharmacokinetic variables of a HCV NS3/4a protease inhibitor of formula (I) selected from $t_{1/2}$, $C_{min}$, $C_{max}$, $C_{ss}$, AUC at 12 hours, or AUC at 24 hours; with the proviso that said use is not practised in the human or animal body.

The term "individual" as used herein refers to an animal, preferably a mammal, most preferably a human, who has been the object of treatment, observation or experiment.

Bioavailability is defined as the fraction of administered dose reaching systemic circulation. $t_{1/2}$ represents the half life or time taken for the plasma concentration to fall to half its original value. $C_{ss}$ is the steady state concentration, i.e. the concentration at which the rate of input of drug equals the rate of elimination. $C_{min}$ is defined as the lowest (minimum) concentration measured during the dosing interval. $C_{max}$, represents the highest (maximum) concentration measured during the dosing interval. AUC is defined as the area under the plasma concentration-time curve for a defined period of time.

The combinations of this invention can be administered to humans in dosage ranges specific for each component comprised in said combinations. The components comprised in said combinations can be administered together or separately. The NS3/4a protease inhibitors of formula (I) or any subgroup thereof, and ritonavir or a pharmaceutically acceptable salt or ester thereof, may have dosage levels of the order of 0.02 to 5.0 grams-per-day.

When the HCV NS3/4a protease inhibitor of formula (I) and ritonavir are administered in combination, the weight ratio of the HCV NS3/4a protease inhibitor of formula (I) to ritonavir is suitably in the range of from about 40:1 to about 1:15, or from about 30:1 to about 1:15, or from about 15:1 to about 1:15, typically from about 10:1 to about 1:10, and more typically from about 8:1 to about 1:8. Also useful are weight ratios of the HCV NS3/4a protease inhibitors of formula (I) to ritonavir ranging from about 6:1 to about 1:6, or from about 4:1 to about 1:4, or from about 3:1 to about 1:3, or from about 2:1 to about 1:2, or from about 1.5:1 to about 1:1.5. In one aspect, the amount by weight of the HCV NS3/4a protease inhibitors of formula (I) is equal to or greater than that of ritonavir, wherein the weight ratio of the HCV NS3/4a protease inhibitor of formula (I) to ritonavir is suitably in the range of from about 1:1 to about 15:1, typically from about 1:1 to about 10:1, and more typically from about 1:1 to about 8:1. Also useful are weight ratios of the HCV NS3/4a protease inhibitor of formula (I) to ritonavir ranging from about 1:1 to about 6:1, or from about 1:1 to about 5:1, or from about 1:1 to about 4:1, or from about 3:2 to about 3:1, or from about 1:1 to about 2:1 or from about 1:1 to about 1.5:1.

The term "therapeutically effective amount" as used herein means that amount of active compound or component or pharmaceutical agent that elicits the biological or medicinal response in a tissue, system, animal or human that is being sought, in the light of the present invention, by a researcher, veterinarian, medical doctor or other clinician, which includes alleviation of the symptoms of the disease being treated. Since the instant invention refers to combinations comprising two or more agents, the "therapeutically effective amount" is that amount of the agents taken together so that the combined effect elicits the desired biological or medicinal response. For example, the therapeutically effective amount of a composition comprising (a) the compound of formula (I) and (b) ritonavir, would be the amount of the compound of formula (I) and the amount of ritonavir that when taken together have a combined effect that is therapeutically effective.

In general it is contemplated that an antiviral effective daily amount would be from 0.01 mg/kg to 500 mg/kg body weight, more preferably from 0.1 mg/kg to 50 mg/kg body weight. It may be appropriate to administer the required dose as one, two, three, four or more (sub-)doses at appropriate intervals throughout the day. Said (sub-)doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

According to one embodiment, the HCV NS3/4a protease inhibitor of formula (I) and ritonavir may be co-administered once or twice a day, preferably orally, wherein the amount of the compounds of formula (I) per dose is from about 1 to about 2500 mg, and the amount of ritonavir per dose is from 1 to about 2500 mg. In another embodiment, the amounts per dose for once or twice daily co-administration are from about 50 to about 1500 mg of the compound of formula (I) and from about 50 to about 1500 mg of ritonavir. In still another embodiment, the amounts per dose for once or twice daily co-administration are from about 100 to about 1000 mg of the compound of formula (I) and from about 100 to about 800 mg of ritonavir. In yet another embodiment, the amounts per dose for once or twice daily co-administration are from about 150 to about 800 mg of the compound of formula (I) and from about 100 to about 600 mg of ritonavir. In yet another embodiment, the amounts per dose for once or twice daily co-administration are from about 200 to about 600 mg of the compound of formula (I) and from about 100 to about 400 mg of ritonavir. In yet another embodiment, the amounts per dose for once or twice daily co-administration are from about 200 to about 600 mg of the compound of formula (I) and from about 20 to about 300 mg of ritonavir. In yet another embodiment, the amounts per dose for once or twice daily co-administration are from about 100 to about 400 mg of the compound of formula (I) and from about 40 to about 100 mg of ritonavir.

Exemplary combinations of the compound of formula (I) (mg)/ritonavir (mg) for once or twice daily dosage include 50/100, 100/100, 150/100, 200/100, 250/100, 300/100, 350/100, 400/100, 450/100, 50/133, 100/133, 150/133, 200/133, 250/133, 300/133, 50/150, 100/150, 150/150, 200/150, 250/150, 50/200, 100/200, 150/200, 200/200, 250/200, 300/200, 50/300, 80/300, 150/300, 200/300, 250/300, 300/300, 200/600, 400/600, 600/600, 800/600, 1000/600, 200/666, 400/666, 600/666, 800/666, 1000/666, 1200/666, 200/800, 400/800, 600/800, 800/800, 1000/800, 1200/800, 200/1200, 400/1200, 600/1200, 800/1200, 1000/1200, and 1200/1200. Other exemplary combinations of the compound of formula (I) (mg)/ritonavir (mg) for once or twice daily dosage include 1200/400, 800/400, 600/400, 400/200, 600/200, 600/100, 500/100, 400/50, 300/50, and 200/50.

In one embodiment of the present invention there is provided an article of manufacture comprising a composition effective to treat an HCV infection or to inhibit the NS3 protease of HCV; and packaging material comprising a label which indicates that the composition can be used to treat infection by the hepatitis C virus; wherein the composition comprises a compound of the formula (I) or any subgroup thereof, or the combination as described herein.

Another embodiment of the present invention concerns a kit or container comprising a compound of the formula (I) or any subgroup thereof, or a combination according to the invention combining an HCV NS3/4a protease inhibitor of formula (I) or a pharmaceutically acceptable salt thereof, and ritonavir or a pharmaceutically acceptable salt thereof, in an amount effective for use as a standard or reagent in a test or assay for determining the ability of potential pharmaceuticals to inhibit HCV NS3/4a protease, HCV growth, or both. This aspect of the invention may find its use in pharmaceutical research programs.

The compounds and combinations of the present invention can be used in high-throughput target-analyte assays such as those for measuring the efficacy of said combination in HCV treatment.

EXAMPLES

The following examples are intended to illustrate the present invention and not to limit it thereto.

Example 1

Preparation of N-[18-[2-(4-isopropylthiazol-2-yl)-7-methoxyquinolin-4-yl-oxy]-2,15-dioxo-3,14,16-triazatricyclo[14.3.0.0$^{4,6}$]nonadec-7-ene-4-carbonyl]-(cyclopropyl)sulfonamide, with the specific stereochemistry as depicted in compound (9) below

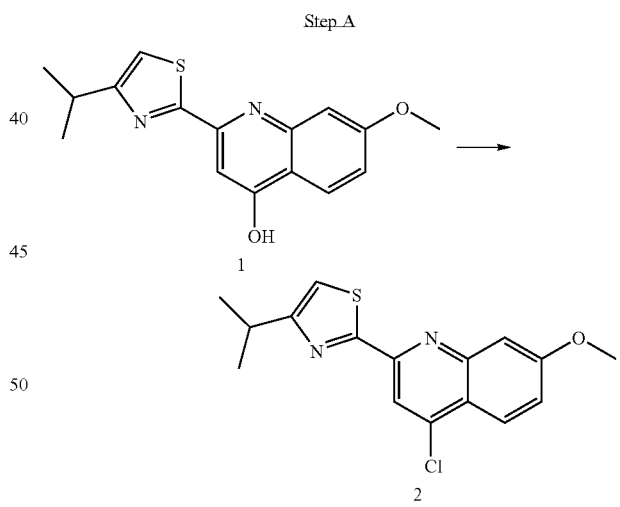

A solution of 2-(4-isopropylthiazol-2-yl)-7-methoxyquinolin-4-ol (1, 3.6 g) in phosphorus oxychloride (20 mL) was heated at 100° C. for 40 min (reaction was monitored by LC-MS). Then, the reaction was cooled down to room temperature and the excess of phosphorus oxychloride was evaporated. The residual oil was partitioned between a saturated solution of NaHCO$_3$ and extracted with diethylether (3×70 mL). The combined organic extracts were washed with brine, dried over MgSO$_4$, concentrated by rotary evaporation and passed through short pad of silica (hexanes) to give 3.6 g (62%) of the desired product 2 as white powder.

Step B

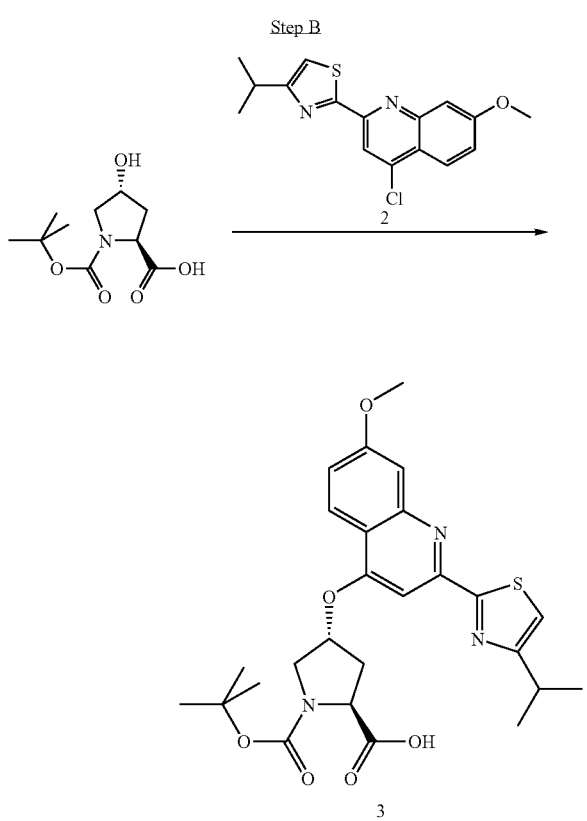

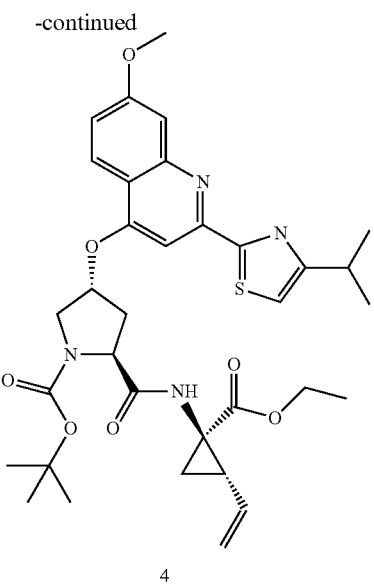

To a stirred solution of Boc-4-hydroxyproline, with the specific stereochemistry as illustrated in the formula above, (2.6 g, 11.2 mmol) in DMSO (80 mL) was added potassium tert-butoxide (3.8 g, 3 eq). After approximately 1 h of stirring 4-chloro-2-(4-isopropylthiazol-2-yl)-7-methoxyquinoline (2, 3.6 g, 11.2 mmol) was added and the reaction mixture was stirred at room temperature overnight. Then, the reaction mixture was diluted with water (350 mL) and neutralized with 1N HCl. The resulting suspension was extracted into ethylacetate (3×100 mL), washed with brine and dried over MgSO$_4$. Filtration and concentration by rotary evaporation gave after drying overnight on high vacuum 3.6 g (62%) of the desired product 3: Purity by HPLC>95%, m/z=514 (M+H)$^+$.

The acid 3 (3.6 g, 7 mmol) was mixed with the 1-amino-2-vinyl-cyclopropane-carboxylic acid ethyl ester hydrochloride, with the specific stereochemistry as illustrated in the formula above, (1.47 g, 7.6 mmol), and then dissolved in DMF. The reaction mixture was flushed with argon and cooled down in an ice bath and DIPEA (1.5 mL) was added in one portion. Then, the reaction mixture was stirred for 10-15 min at 0° C., before HATU (2.93 g, 7.7 mmol) was added at 0° C. under argon, in one portion. After 40 min at 0° C. (reaction was monitored by LC-MS), the reaction mixture was concentrated by rotary evaporation (not to complete dryness), then mixed with a solution of saturated NaHCO$_3$ and extracted into EtOAc (3×100 mL). The organic layer was washed with brine, dried over MgSO$_4$ and concentrated by rotary evaporation. Purification by column chromatography on silica (DCM) and then on YMC silica (200 g, gradient hexanes/EA 3:2 to 2:3) afforded 3.81 g (84%) of the target product 4 as a white powder.

Step C

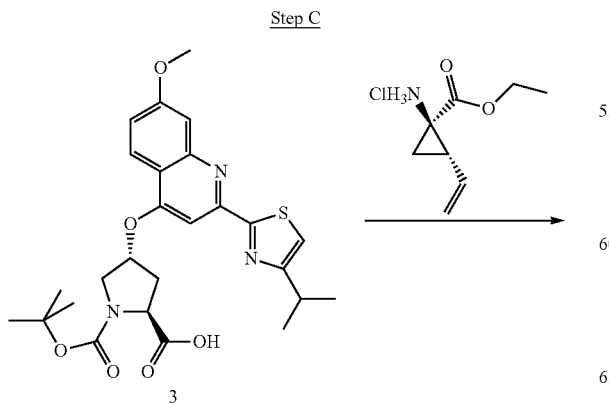

Step D

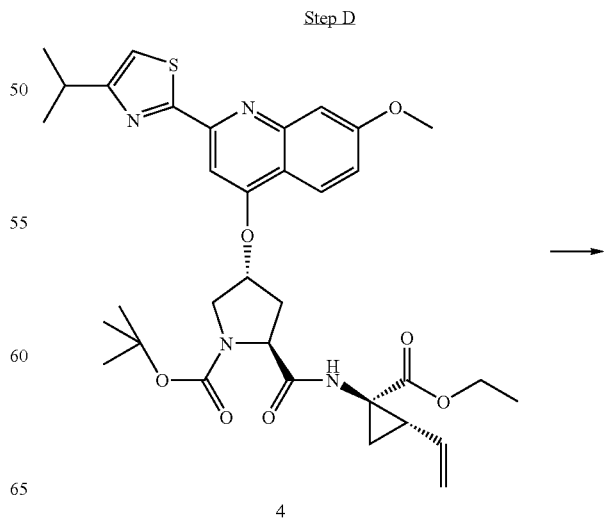

-continued

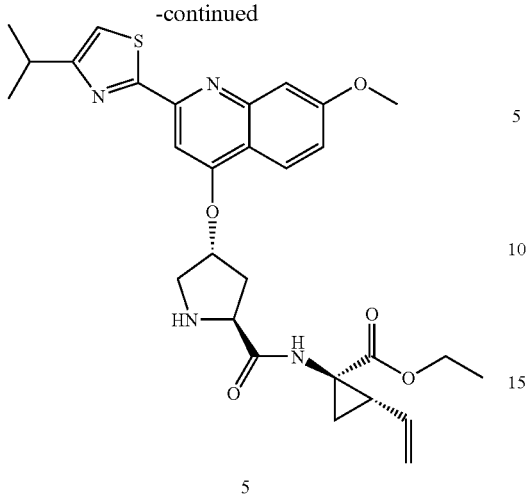

5

A solution of 4 (3.81 g, 5.8 mmol) in CH₂Cl₂ (30 mL) and trifluoroacetic acid (30 mL) was stirred at room temperature for about 1.5 h. Then, the solvent was evaporated and the residue partitioned between saturated NaHCO₃ (100 mL) and diethylether (3×100 mL). The diethylether layers were combined, washed with brine, dried over MgSO₄ and evaporated to give 3.13 g (98.3%) of the target product 5: m/z=551 (M+H)⁺.

Step E

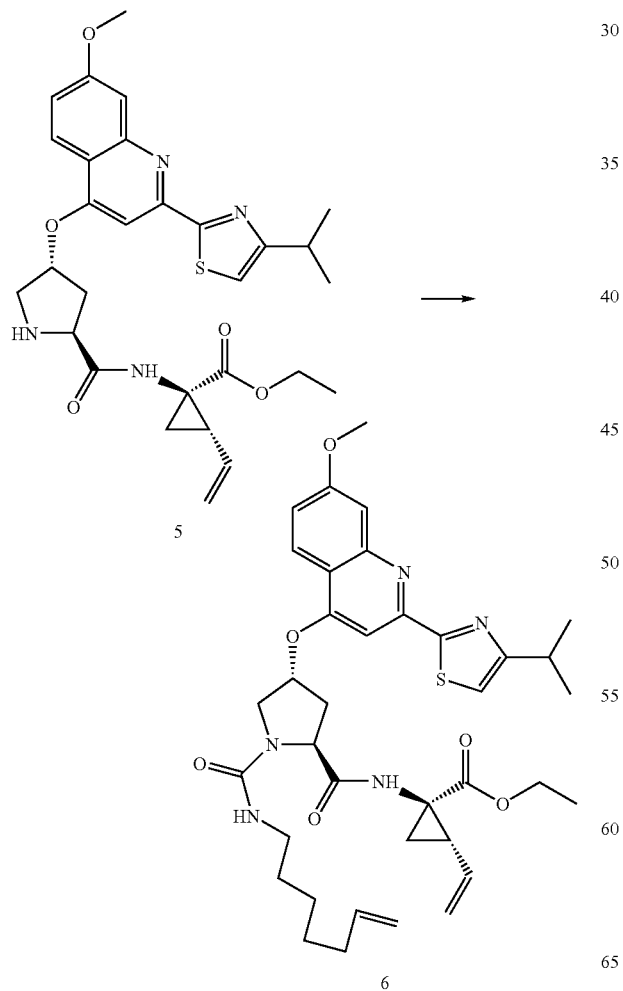

NaHCO₃ (1.0 g) was added to a solution of 5 (1.4 g, 2.5 mmol) in tetrahydrofuran (50 mL). Then, phosgene (5 mL, 1.9 M in toluene) was added at 0° C. under argon. The resulting suspension was stirred for 40 min at room temperature (monitoring with LC-MS). Then, the reaction mixture was filtered and washed with THF (2×30 mL). The filtrate was concentrated by rotary evaporation and re-dissolved in CH₂Cl₂ (50 mL). NaHCO₃ (1.0 g) and N-methylhept-6-enylamine (1.5 g, 13 mmol) was added. The reaction mixture was stirred at room temperature overnight, and then filtered. Purification by chromatography on silica gel (ether) provided 1.42 g (84%) of the target product 6: m/z=690 (M+H)⁺.

Step F

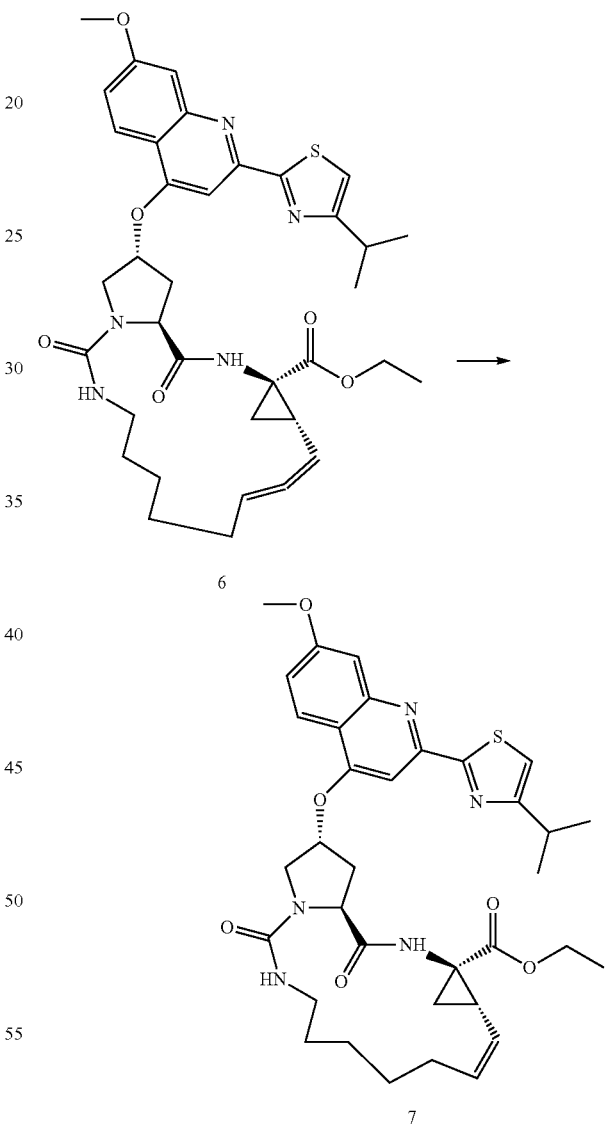

A solution of 6 (1.42 g, 2 mmol) in dry dichloroethane (900 mL, 0.0023M solution) was bubbled with argon for approximately 15 min. Then, Hoveyda-Grubbs 1ˢᵗ generation catalyst (120 mg, 12 mol %) was added and the reaction mixture was heated at reflux under stirring with a slow flow of argon for 16 h. The reaction mixture was then cooled to room temperature and MP-TMT palladium scavenger (approximately 200 mg)

was added to the mixture. After 2.5 h, the scavenger was removed by filtration and washed with 50 mL CH$_2$Cl$_2$. The solution obtained was concentrated by rotary evaporation. The residue was purified by column chromatography on YMC silica (100 g, EtOAc/hexane 1:1) to give 806 mg (57%) of the target product 7: m/z=662 (M+H)$^+$.

Step G

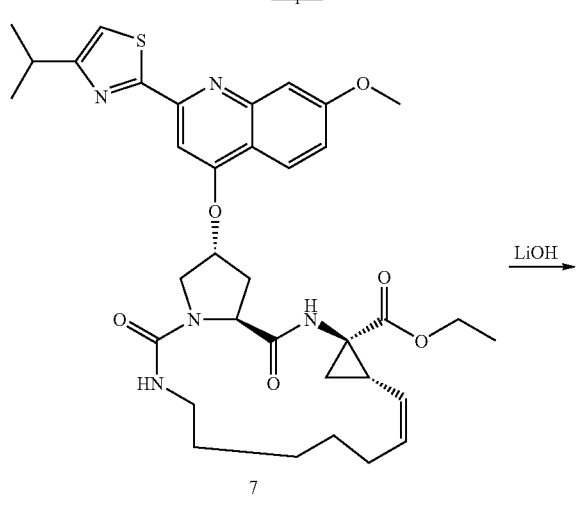

7

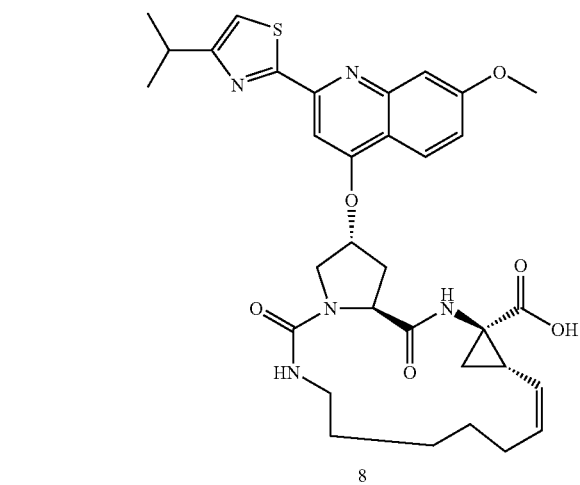

8

Lithium hydroxide (300 mg) in water (6 mL) was added to a solution of the macrocyclic ester 7 (806 mg, 2.1 mmol) in tetrahydrofuran (12 mL) and methanol (6 mL). After 1 h at 50° C., the volume was reduced to half by evaporation and water (30 mL) was added. Acidification (pH=2) followed by extraction with chloroform gave 760 mg of the target product 8 as a white powder: m/z=662 (M+H)$^+$.

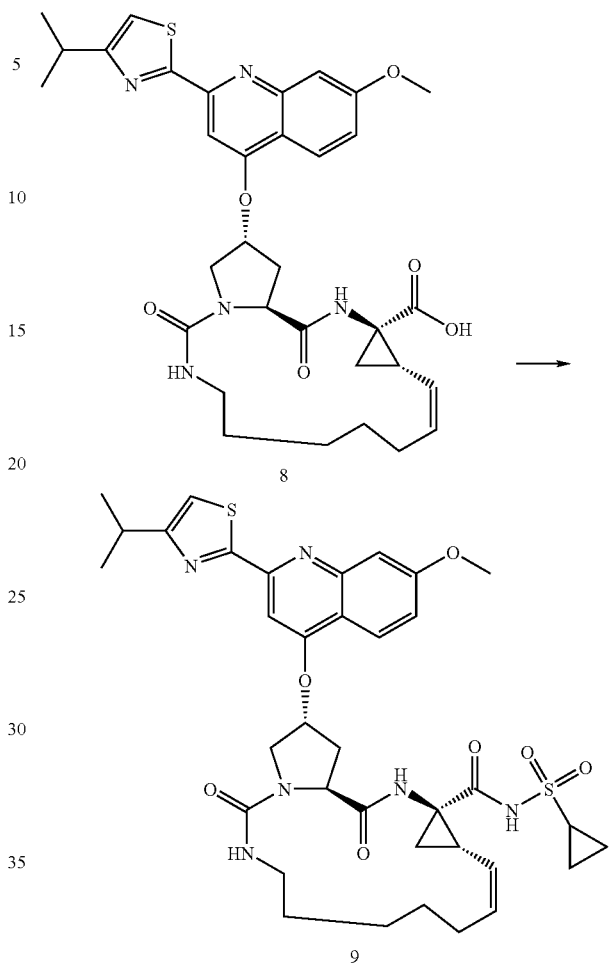

A solution of acid 8 (760 mg, 1.2 mmol) and CDI (389 mg, 2.4 mmol, 2 eq) in dry THF (10 mL) was heated at reflux for 2 h under N$_2$. Optionally the azalactone derivative, if desired, can be isolated. The reaction mixture was cooled to room temperature and a mixture of sulfonamide, prepared as described in WO03/053349, (436 mg, 3.6 mmol, 3 eq) and DBU (0.5 mL, 3 mmol) in dry THF (10 mL) was added. The resulting solution was heated at 55° C. for 18 h (monitored by LC-MS). Then, the reaction mixture was cooled down to room temperature, the solvent was evaporated and the residue partitioned between EtOAc and water (pH adjusted to 3.0 with HCl). The crude material was purified by column chromatography (EtOAc/Petroleum ether 1:1) to give 380 mg of the target product contaminated with up to 20% of starting sulfonamide (NMR determination). This material was purified by column chromatography on prepacked column (gradient ether to ether/THF, 3:1). Third purification by column chromatography (YMC silica 50 g, ether, followed with ether-methanol 9:1) provided 176 mg of the title compound as a slightly yellow powder, which was further purified by prep HPLC to give 55 mg of the title product as a yellowish powder. m/z=737, (M+H)$^+$, NMR data (125 MHz, CDCl$_3$): $^{13}$C, δ 6.3, 6.5, 6.9, 22.0, 22.7, 22.8, 25.4, 26.7, 28.6, 29.1, 29.7, 31.3, 32.7, 34.7, 38.4, 45.3, 51.8, 55.8, 60.1, 77.0, 96.7, 107.5, 114.7, 116.5, 119.4, 123.2, 125.8, 136.4, 151.4, 153.1, 157.7, 160.2, 161.8, 165.5, 168.2, 168.7, 178.2.

Example 2

Synthesis of N-[17-(2-(4-isopropylthiazol-2-yl)-7-methoxyquinolin-4-yl-oxy)-13-methyl-2,14-dioxo-3,13,15-triazatricyclo[13.3.0.0$^{4,6}$]octadec-7-ene-4-carbonyl](cyclopropyl)sulfonamide, with the specific stereochemistry as depicted in compound (16) below.

Procedure A:

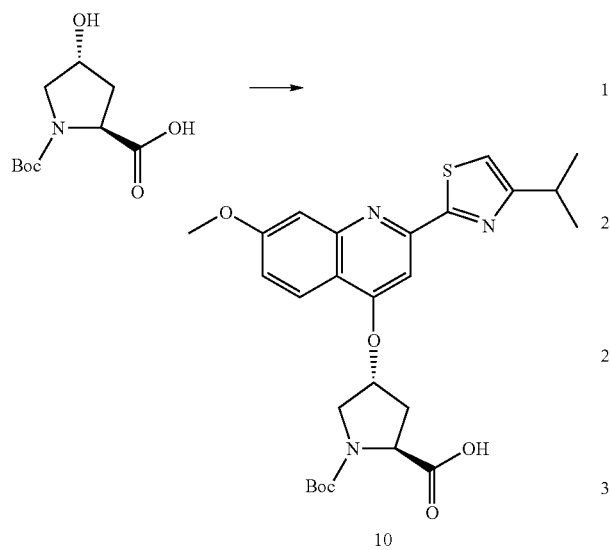

Step A

To a stirred solution of BOC-4-hydroxyproline, with the specific stereochemistry as illustrated in the formula above, (2.59 g, 11.2 mmol) in DMSO (80 mL) was added potassium-tert-butoxide (3.77 g, 33.6 mmol). After 1 hr of stirring at room temperature, the quinoline chloride 2 (3.57 g, 11.2 mmol) was added and the solution was stirred at room temperature overnight. The mixture was diluted with H$_2$O (350 mL), washed with EtOAc (100 mL), and acidified to ca. pH 3 with 1 M HCl. The resulting suspension was extracted with EtOAc (3×100 mL), washed with brine, and dried over MgSO$_4$. After evaporation compound 10 (3.60 g, 62%) was afforded.

Step B

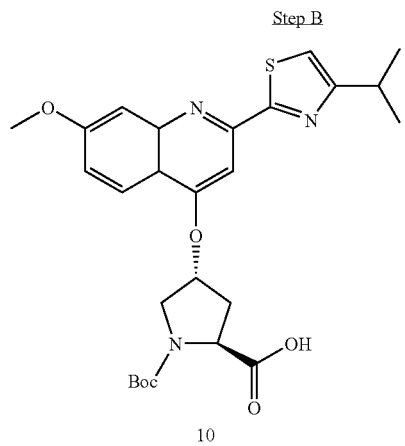

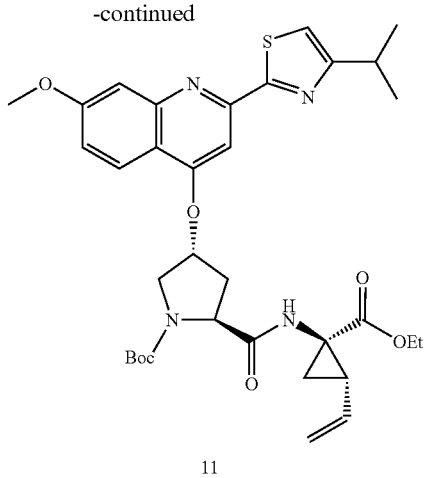

Compound 10 (3.60 g, 7.02 mmol) was dissolved in DMF (20 mL). Then, 1-amino-2-vinyl-cyclopropanecarboxylic acid ethyl ester hydrochloride (1.47 g, 7.68 mmol) was added, and the reaction mixture was flushed with argon and cooled to 0° C. DIPEA (3.00 mL, 17.2 mmol) and HATU (2.93 g, 7.66 mmol) were added and the reaction mixture was stirred for 40 min at 0° C. The solution was evaporated, mixed with saturated NaHCO$_3$, and extracted with EtOAc (3×100 mL). The combined organic layers were washed with brine, dried over MgSO$_4$, and evaporated. Flash column chromatography (hexanes/EtOAc 3:2→hexanes/EtOAc 2:3) provided compound 11 (3.81 g, 84%) as a white powder.

Step C

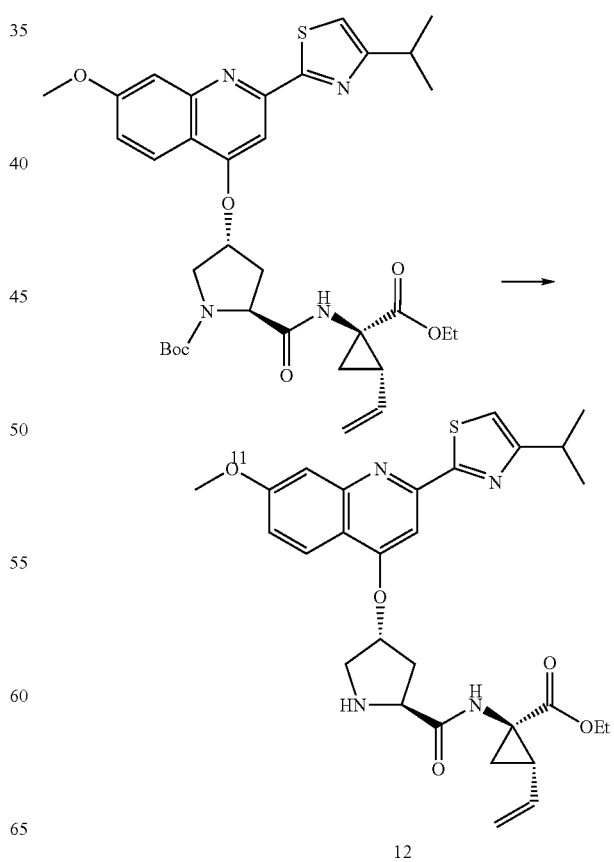

A solution of 11 (3.81 g, 5.86 mmol) in CH$_2$Cl$_2$ (30 mL) and TFA (30 mL) was stirred at room temperature for 1.5 h. The volatiles were then evaporated. Saturated NaHCO$_3$ (100 mL) was added to the oil obtained and the slurry was extracted with diethylether (3×100 mL). The organic layers were combined, washed with brine, dried over MgSO$_4$, and evaporated to give compound 12 (3.13 g, 98%).

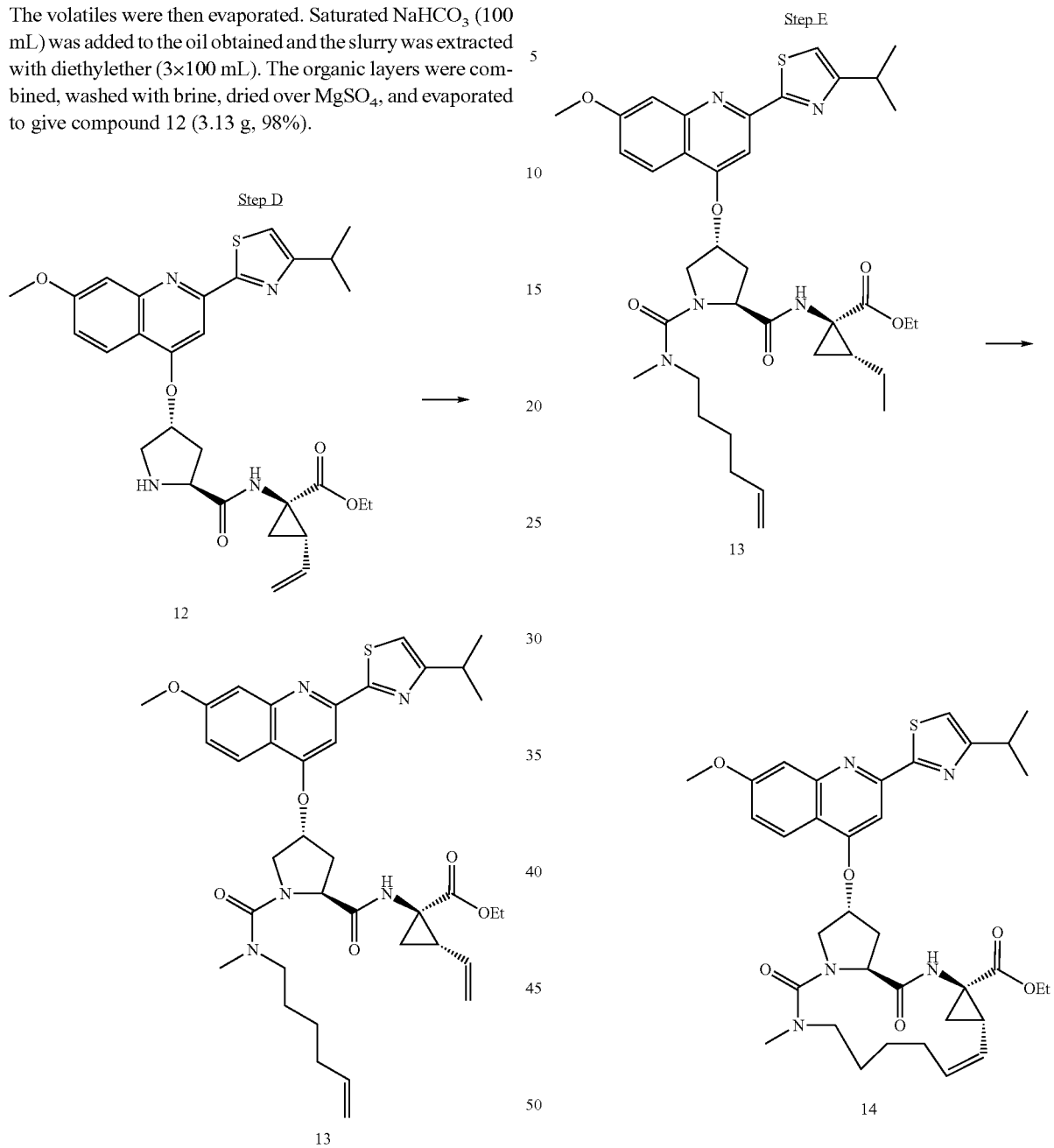

To a solution of compound 12 (1.41 g, 2.56 mmol) in THF (40 mL) were added NaHCO$_3$ (4 tablespoons) and phosgene in toluene (1.93 M, 4.0 mL, 7.7 mmol). The mixture was vigorously stirred for 1 h at room temperature, after which it was filtered and evaporated. The residue was dissolved in CH$_2$Cl$_2$ (40 mL), and NaHCO$_3$ (3 tablespoons) and hex-5-enyl-methylamine hydrochloride (770 mg, 5.15 mmol) were added. After stirring overnight at room temperature, the reaction mixture was filtered, ca. 3 g of silica was added, and the slurry was evaporated to dryness. Flash column chromatography (diethylether→3% methanol in diethylether) afforded compound 13 (1.57 g, 89%) as a slightly yellow powder.

Compound 13 (1.53 g, 2.18 mmol) was dissolved in 1,2-dichloroethane (1.50 L) and the solution was degassed with N$_2$. Hoveyda Grubbs catalyst 1$^{st}$ generation (95 mg, 0.16 mmol) was added and the mixture was refluxed overnight under N$_2$. The solution was allowed to cool to 60° C., after which 1 tablespoon of the scavenger MP-TMT was added. The reaction mixture was stirred for 3 h (while cooling to room temperature), filtered, and evaporated. The residue was dissolved in CH$_2$Cl$_2$, ca 3 g of silica was added, and the slurry was evaporated to dryness. After flash column chromatography (diethylether→3% methanol in diethylether) compound 14 (1.09 g, 74%) was obtained as white prisms.

Step F

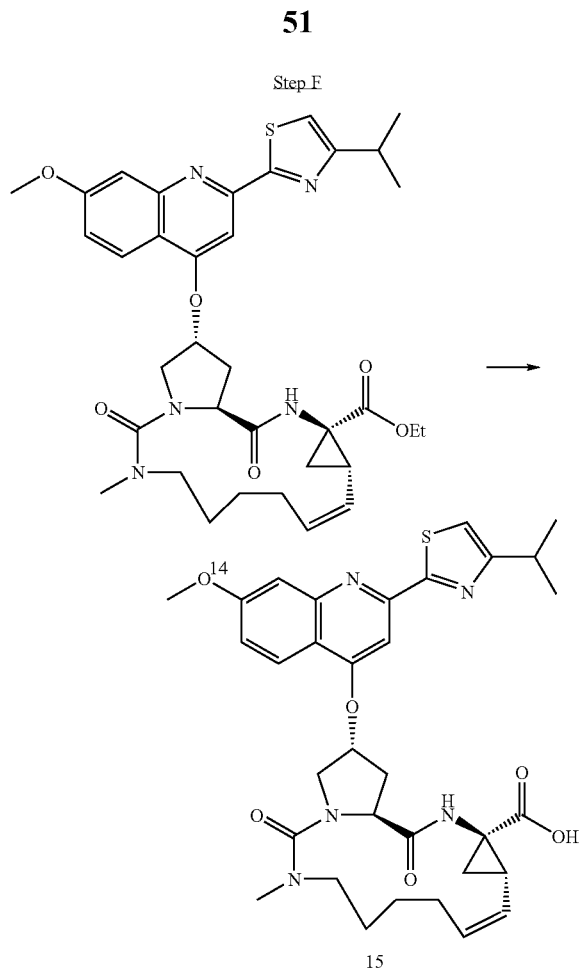

Compound 14 (1.00 g, 1.51 mmol) was dissolved in THF/methanol/H₂O 2:1:1 (200 mL). An aqueous solution of LiOH (1 M, 15.1 mL, 15.1 mmol) was added dropwise at room temperature over 10 min, and the resulting reaction mixture was stirred at room temperature for 20 h. The solution was acidified to ca. pH 1 with 1 M HCl, and concentrated until almost all of the THF and methanol had been removed. The resulting slurry was extracted with CH₂Cl₂ four times, and the organic phases were pooled, dried (MgSO₄), and evaporated to give compound 15 (960 mg, 100%) as a slightly yellow powder.

Step G

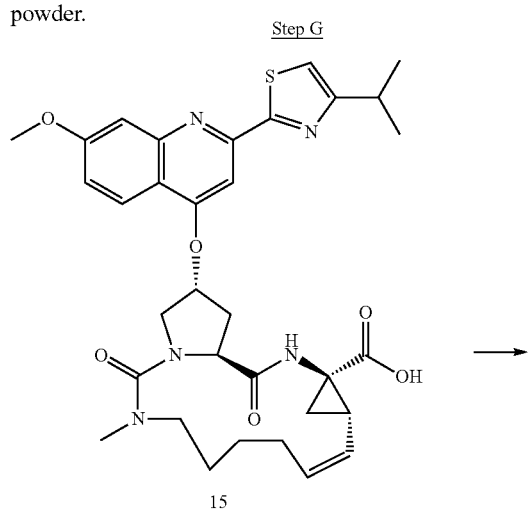

-continued

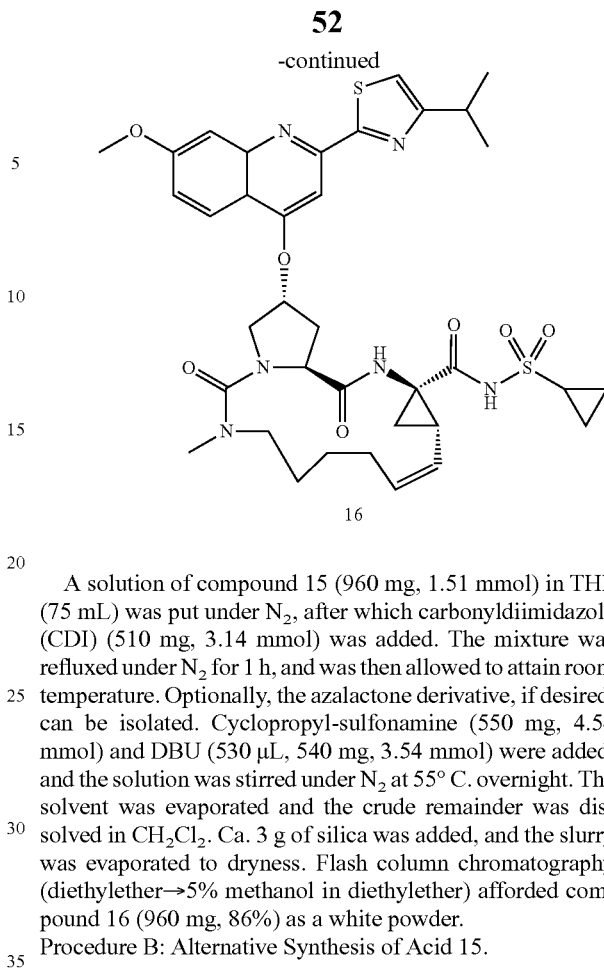

A solution of compound 15 (960 mg, 1.51 mmol) in THF (75 mL) was put under N₂, after which carbonyldiimidazole (CDI) (510 mg, 3.14 mmol) was added. The mixture was refluxed under N₂ for 1 h, and was then allowed to attain room temperature. Optionally, the azalactone derivative, if desired, can be isolated. Cyclopropyl-sulfonamine (550 mg, 4.54 mmol) and DBU (530 µL, 540 mg, 3.54 mmol) were added, and the solution was stirred under N₂ at 55° C. overnight. The solvent was evaporated and the crude remainder was dissolved in CH₂Cl₂. Ca. 3 g of silica was added, and the slurry was evaporated to dryness. Flash column chromatography (diethylether→5% methanol in diethylether) afforded compound 16 (960 mg, 86%) as a white powder.

Procedure B: Alternative Synthesis of Acid 15.

Step A

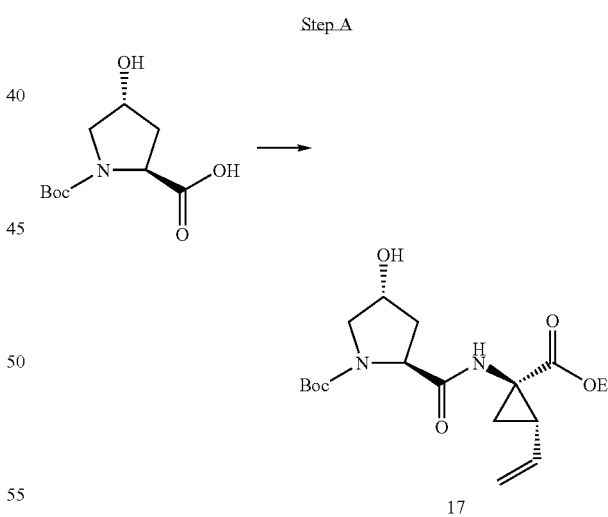

Boc-protected 4-hydroxyproline (10.2 g, 44.1 mmol), HATU (18.7 g, 49.2 mmol) and the cyclopropyl ester (9.31 g, 48.6 mmol), both with the specific stereochemistry as illustrated in the formulae above, were dissolved in DMF (120 mL) and cooled to 0° C. Diisopropylethylamine (DIPEA) (30.0 mL, 172 mmol) was added. The solution was allowed to warm up to room temperature and was stirred overnight. CH₂Cl₂ (~80 mL) was added and the reaction mixture was washed with saturated aqueous NaHCO₃, citric acid, H₂O, and brine and was then dried (MgSO₄). Ca. 30 g of silica was added and the slurry was evaporated to dryness. Purification by flash column chromatography (diethylether→7% methanol in diethylether) gave compound 17 (13.0 g, 80%) as a white powder.

Step B

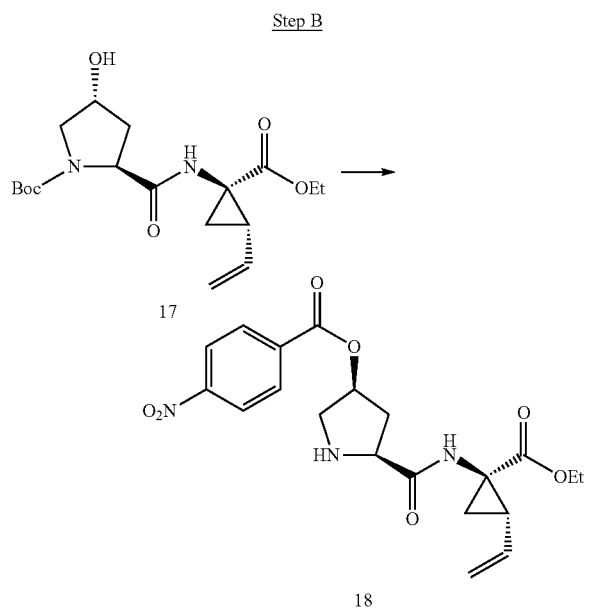

Compound 17 (8.11 g, 22.0 mmol), p-nitrobenzoic acid (5.51 g, 33.0 mmol) and Ph₃P (8.66 g, 33.0 mmol) were dissolved in THF (100 mL). The solution was cooled to 0° C. and DIAD (6.50 mL, 33.0 mmol) was added dropwise. The reaction mixture was allowed to warm up to room temperature and was stirred overnight. Saturated aqueous NaHCO₃ (60 mL) was added and the mixture was extracted with CH₂Cl₂ several times. The organic phases were pooled and dried (MgSO₄), after which ca. 40 g of silica was added and the slurry was evaporated to dryness. Purification by flash column chromatography (pentane/diethylether 2:1→pentane/diethylether 1:2→2% methanol in diethylether) gave the Boc-protected intermediate (9.50 g, 83%) as a white powder. This intermediate (9.50 g, 18.4 mmol) was dissolved in CH₂Cl₂ (66 mL) and the solution was cooled to 0° C. TFA (33 mL) was added dropwise, and the mixture was stirred at room temperature for 2 h. The volatiles were evaporated, CH₂Cl₂ (100 mL) was added, and aqueous Na₂CO₃ (0.50 M) was added until pH ca. 8 was reached. After separation, the organic phase was dried (MgSO₄) and evaporated to give compound 18 (7.68 g, 83%) as a slightly yellow powder.

Step C

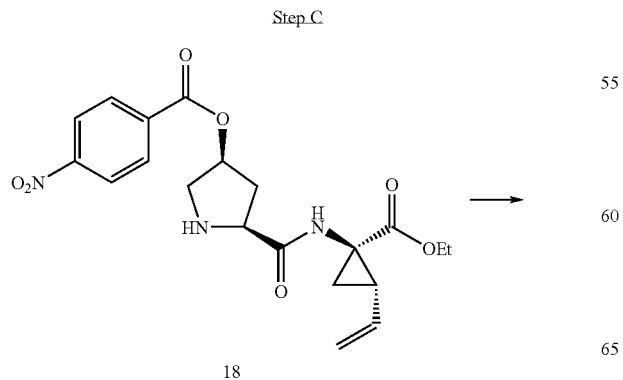

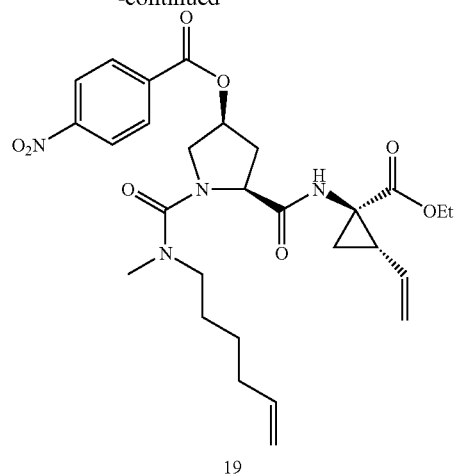

To a solution of compound 18 (6.90 g, 16.5 mmol) in THF (240 mL) were added NaHCO₃ (15 tablespoons) and phosgene in toluene (1.93 M, 18.0 mL, 34.7 mmol). The mixture was vigorously stirred for 1 h at room temperature, after which it was filtered and evaporated. The residue was dissolved in CH₂Cl₂ (250 mL), and NaHCO₃ (15 tablespoons) and hex-5-enyl-methylamine hydrochloride (5.00 g, 33.4 mmol) were added. After stirring overnight at room temperature the reaction mixture was filtered, ca. 17 g of silica was added, and the slurry was evaporated to dryness. Flash column chromatography (diethylether→3% methanol in diethylether) afforded compound 19 (8.00 g, 87%) as a white powder.

Step D

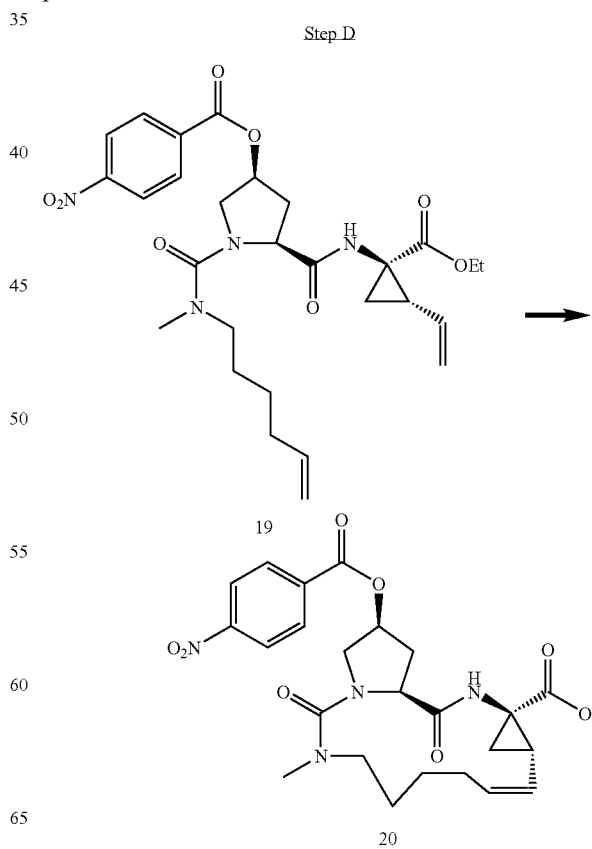

Compound 19 (1.61 g, 2.90 mmol) was dissolved in 1,2-dichloroethane (1.50 L) and the solution was degassed with N₂. Hoveyda Grubbs catalyst 1st generation (125 mg, 0.21 mmol) was added and the mixture was refluxed overnight under N₂. The solution was allowed to cool to 60° C., after which 1 tablespoon of the scavenger MP-TMT was added. The reaction mixture was stirred for 3 h (while cooling to room temperature), filtered, and evaporated. The residue was dissolved in CH₂Cl₂, ca. 3 g of silica was added, and the slurry was evaporated to dryness. After flash column chromatography (diethylether→3% methanol in diethylether) compound 20 (1.13 g, 74%) was obtained as a grayish powder.

Step E

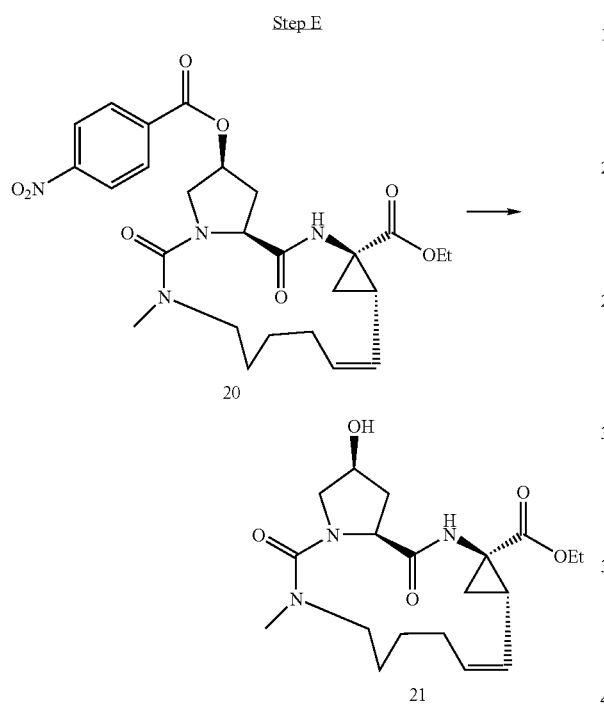

Compound 20 (200 mg, 0.38 mmol) was dissolved in a mixture of THF/methanol/water (2:1:1, 20 mL) and cooled in an ice-bath. Aqueous LiOH (1 M, 1.9 ml, 1.9 mmol) was added slowly. The mixture was stirred at 0° C. for 4 h, and was then neutralized with 1 M HCl and extracted with CH₂Cl₂. The organic layer was washed with saturated aqueous NaHCO₃, H₂O, and brine. After drying (MgSO₄) and evaporation, the crude remainder was purified by flash column chromatography (2% methanol in CH₂Cl₂→4% methanol in CH₂Cl₂) to give compound 21 (115 mg, 80%) as a grayish powder.

Step F

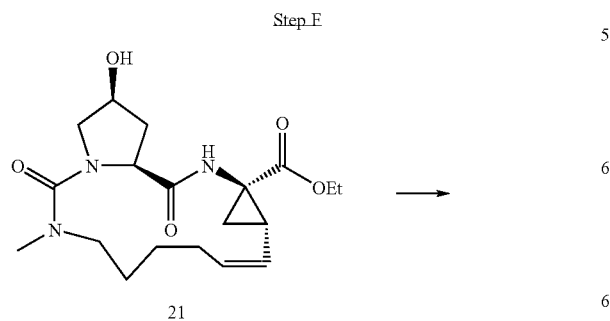

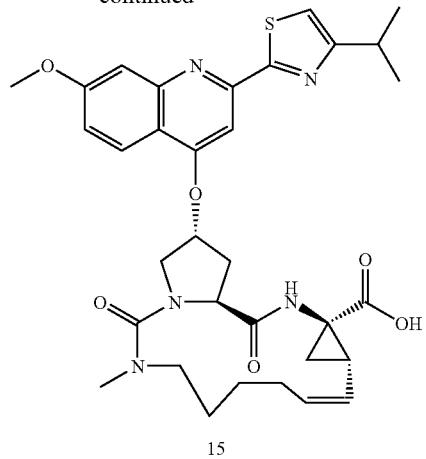

Compound 21 (100 mg, 0.26 mmol), Ph₃P (100 mg, 0.38 mmol) and 2-(4-isopropyl-thiazol-2-yl)-7-methoxyquinolin-4-ol (1) (117 mg, 0.39 mmol) were mixed in THF (10-15 mL), and the slurry was cooled to 0° C. in an ice-bath. DIAD (77 μL, 0.39 mmol) was added dropwise. The ice-bath was then removed and the mixture was stirred at room temperature for 12 h. The solvent was evaporated and the crude product was dissolved in THF/methanol/H₂O 2:1:1 (12 mL). Aqueous LiOH (1 M, 3.80 mL, 3.80 mmol) was added and the mixture was stirred at room temperature overnight. The volume was doubled by the addition of water and the slurry was extracted with diethylether. The aqueous phase was acidified to pH ca. 1 with 1 M HCl and extracted with CH₂Cl₂. The CH₂Cl₂ phase was dried (MgSO₄) and evaporated. The desired product was obtained by flash column chromatography (2% methanol in diethylether until the excess quinoline 1 eluted, and then 10% methanol in CH₂Cl₂) to give compound 15 (71 mg, 42%).

Example 3

Preparation of Cyclopropanesulphonic acid {17-[2-(4-isopropylthiazol-2-yl)-7-methoxyquinolin-4-yloxy]-2,14-dioxo-3,13,15-triaza-tricyclo[13.3.0.0⁴,⁶]-octadec-7-ene-4-carbonyl}-amide, with the specific stereochemistry as depicted in compound (26) below

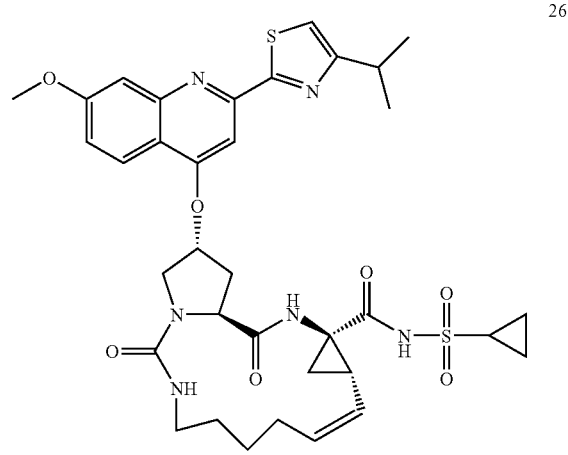

Step A: Preparation of 1-({1-[Hex-5-enyl-(4-methoxybenzyl)-carbamoyl]-4-[2-(4-isopropylthiazol-2-yl)-7-methoxyquinolin-4-yloxy]-pyrrolidine-2-carbonyl}-amino)-2-vinyl-cyclopropane carboxylic acid ethyl ester, with the specific stereochemistry as depicted in compound (22) below

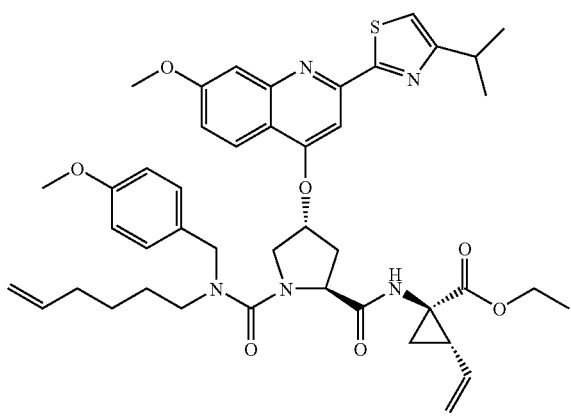

22

Compound 5, prepared in Example 1, step D (1.97 g, 3.58 mmol) was mixed with ca. 200 mg NaHCO₃ (2 small spoons) and THF (20 ml). 3 ml 1.9M Phosgene in toluene was added to the reaction mixture and the reaction mixture was stirred for about 1.5 h at room temperature. The reaction was monitored by LC-MS. Starting material disappeared and the peak of the chlorocarbonyl intermediate (>90% according to LC-MS data) was formed. The reaction mixture was filtered and concentrated by rotary evaporation. Then it was dissolved in CH₂Cl₂ and hex-5-enyl-(p-methoxy-benzyl)amine (0.9 g) was added together with 100-150 mg (1 spoon) of NaHCO₃. The reaction mixture was stirred at room temperature overnight and then filtrated and purified by column chromatography on silica (EtOAc/petroleum ether) to give the pure title compound 22 (1.42 g, 84%). MS (M⁺) 797.

Step B: Preparation of 17-[2-(4-Isopropylthiazol-2-yl)-7-methoxyquinolin-4-yloxy]-13-(4-methoxybenzyl)-2,14-dioxo-3,13,15-triaza-tricyclo[13.3.0.0⁴,⁶]octadec-7-ene-4-carboxylic acid ethyl ester, with the specific stereochemistry as depicted in compound (23) below

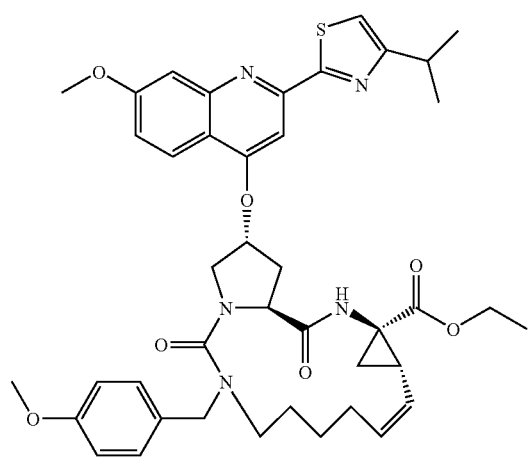

23

Compound 22 (1.68 g, 2.1 mmol) as prepared in step A, was dissolved in dry dichloro-ethane (distilled over CaH, about 800 ml) and bubbled with argon for ca. 10 min. Then the Hoveyda 1$^{st}$ generation catalyst (88 mg, 7 mol %) was added to the solution and the reaction mixture was heated at 100° C. while stirring with slow flow of argon for 16 h. The reaction mixture was then cooled to room temperature and MP-TMT palladium scavenger (ca. 100 mg) was added and the mixture was stirred for 2.5 h. The scavenger was removed by filtration and washed with 100 ml of CH₂Cl₂. The obtained solution was concentrated by rotary evaporation and dried on high vacuum which gave the title compound (m/z=599, (M+H)⁺), HPLC purity 79% (diode array), 95% (ELSD). Yield 63%.

Step C: Preparation of 17-[2-(4-Isopropylthiazol-2-yl)-7-methoxyquinolin-4-yloxy]-13-(4-methoxybenzyl)-2,14-dioxo-3,13,15-triaza-tricyclo[13.3.0.0⁴,⁶]octadec-7-ene-4-carboxylic acid, with the specific stereochemistry as depicted in compound (24) below

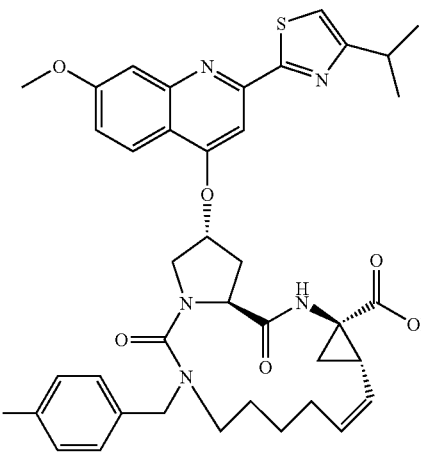

24

Compound 23 (910 mg, 1.2 mmol) as prepared in step B, was dissolved in 30 mL THF, 15 mL methanol and 15 mL H₂O. Aqueous 1M LiOH (10 mL) was added to the solution. The reaction was stirred for 2 h at 50° C., to allow all the starting material to react (checked by LC-MS). The reaction mixture was acidified with citric acid, extracted with chloroform (3×75 mL) and washed with brine. The organic phase was dried with MgSO₄. The crude product was purified by flash chromatography (gradient starting from ethyl acetate/hexane gradient 2:1) to afford the title compound (24) as a slightly yellow solid (864 mg). HPLC purity 96%.

Step D: Preparation of Cyclopropanesulphonic acid [17-[2-(4-isopropylthiazol-2-yl)-7-methoxyquinolin-4-yloxy]-13-(4-methoxybenzyl)-2,14-dioxo-3,13,15-triaza-tricyclo-[13.3.0.0⁴,⁶]octadec-7-ene-4-carbonyl]-amide, with the specific stereochemistry as depicted in compound (25) below

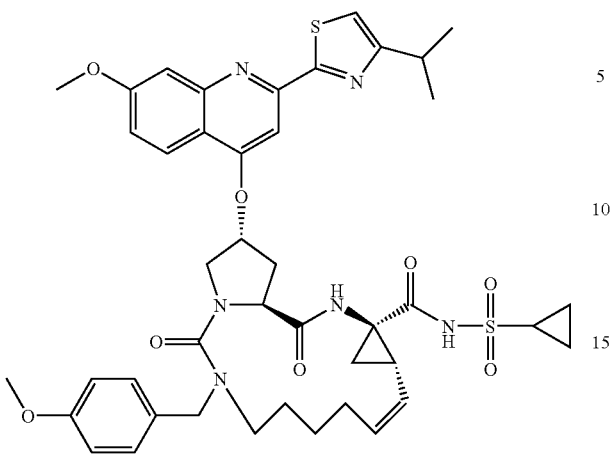

Compound 24 (50 mg, 0.068 mmol, 1 eq) was mixed with CDI (44 mg, 3 eq) and dissolved in THF (1.0 mL) in a 2 ml microwave vial. The cap was attached and the vial flushed with argon. Activation was performed in a microwave for 12 min at 100° C. (normal; no pre-stirring). The reaction was checked by LC-MS (100% conversion to activated intermediate—mass less then substrate: M$^+$-16). Optionally, the azalactone derivative, if desired, can be isolated. Cyclopropyl sulphonamide (49 mg, 4 eq) was mixed with THF and DBU (60 µl, 4 eq) was added in a separate vial. After complete activation, the mixture was added by syringe to the reaction vial. The reaction mixture was heated in a microwave at 100° C. for 1 h. The reaction mixture was concentrated by rotary evaporation, mixed with EtOAc and water, and 1 drop of 3M HCl was added. The water phase was washed with EtOAc (3×15 ml). The combined organic extracts were washed with brine and dried over MgSO$_4$. After filtering off the drying agent and concentration by rotary evaporation, the crude product was purified by column chromatography on YMC silica (~70 mg, ethyl acetate, R$_f$=0.7, starting sulphonamide 0.6). Fractions containing the desired product were combined and concentrated by rotary evaporation to afford the title compound 25 (83 mg, yield 98%) with 86% purity. The compound was used without additional purification in the next step.

Step E: Preparation of Cyclopropanesulphonic acid {17-[2-(4-isopropylthiazol-2-yl)-7-methoxyquinolin-4-yloxy]-2,14-dioxo-3,13,15-triaza-tricyclo[13.3.0.0$^{4,6}$]octadec-7-ene-4-carbonyl}-amide, with the specific stereochemistry as depicted in compound (26) below

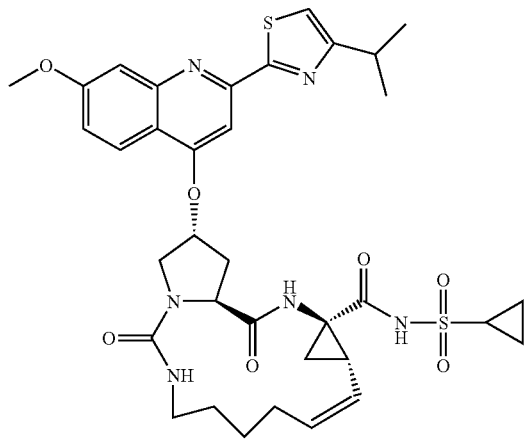

Compound 25 (65 mg, 0.077 mmol) was dissolved in 4 mL DCM. 2 mL TFA was added and the solution was stirred for 20 minutes. The reaction mixture was poured in a reparatory funnel with NaHCO$_3$ and CHCl$_3$. Extractions were made with CHCl$_3$ (3×50 mL) and wash with NaHCO$_3$ (2×50 mL) and brine. The organic phase was dried with MgSO$_4$ and concentrated by rotary evaporation. The crude product was purified with flash chromatography on YMC silica (20 g, diethyl ether) which gave product 26 as a white solid (25 mg, yield 45%).

Example 4

Preparation of 1-Methyl-cyclopropanesulphonic acid [17-[2-(4-isopropyl-thiazol-2-yl)-7-methoxyquinolin-4-yloxy]-2,14-dioxo-3,13,15-triaza-tricyclo-[13.3.0.0$^{4,6}$]octadec-7-ene-4-carbonyl]-amide, with the specific stereochemistry as depicted in compound (28) below

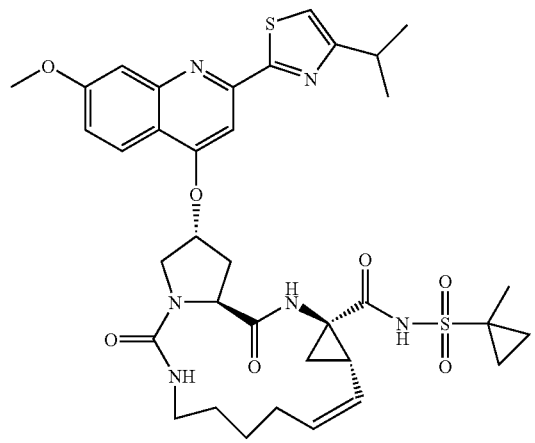

Step A: Preparation of 1-Methyl-cyclopropanesulphonic acid [17-[2-(4-isopropyl-thiazol-2-yl)-7-methoxyquinolin-4-yloxy]-13-(4-methoxybenzyl)-2,14-dioxo-3,13,15-triaza-tricyclo[13.3.0.0$^{4,6}$]octadec-7-ene-4-carbonyl]-amide, with the specific stereochemistry as depicted in compound (27) below

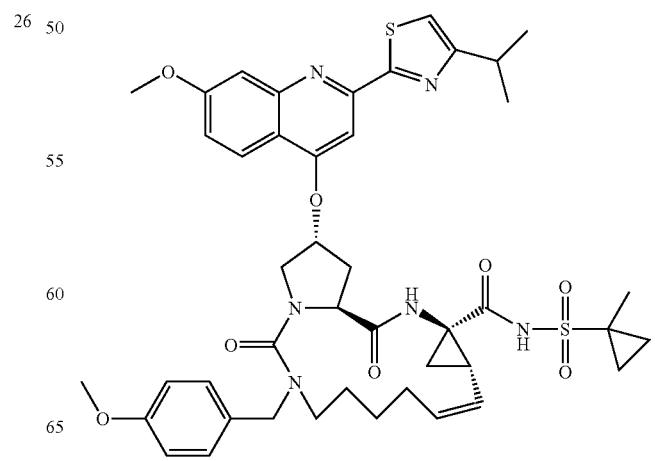

The procedure described in Step D of Example 3, was followed, but using 1-methyl-cyclopropyl sulphonamide instead of cyclopropyl sulphonamide (prepared as described in WO2004/043339), which gave the title compound (27) (24.5 mg, 43%) as white solid after purification by column chromatography on silica (eluent diethyl ether).

Step B: Preparation of 1-Methyl-cyclopropanesulphonic acid [17-[2-(4-isopropyl-thiazol-2-yl)-7-methoxyquinolin-4-yloxy]-2,14-dioxo-3,13,15-triaza-tricyclo-[13.3.0.0$^{4,6}$]octadec-7-ene-4-carbonyl]-amide, with the specific stereochemistry as depicted in compound (28) below

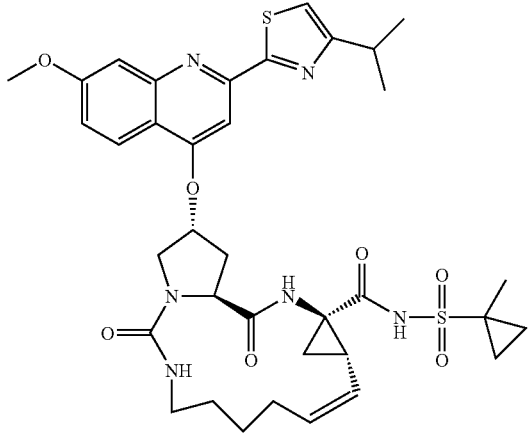

28

Compound 27 (20 mg, 0.023 mmol) was dissolved in 3 ml methylene chloride, 1 ml TFA was added and reaction mixture was stirred at room temperature for 20 min. HPLC showed the absence of starting material. A solution of saturated NaHCO$_3$ (5 ml) was added to the reaction mixture and the resulting mixture was extracted into CH$_2$Cl$_2$. The organic extract was washed with brine, dried over MgSO$_4$ and concentrated by rotary evaporation. The resulting oil was purified by column chromatography on YMC silica (20 g, diethyl ether) which gave the title compound (28) (14.7 mg, 85%) as white powder. HPLC purity>95%.

Example 5

Preparation of 1-Methyl-cyclopropanesulphonic acid [18-[2-(4-isopropyl-thiazol-2-yl)-7-methoxyquinolin-4-yloxy]-2,15-dioxo-3,14,16-triaza-tricyclo-[14.3.0.0$^{4,6}$]nonadec-7-ene-4-carbonyl]-amide, with the specific stereochemistry as depicted in compound (33) below

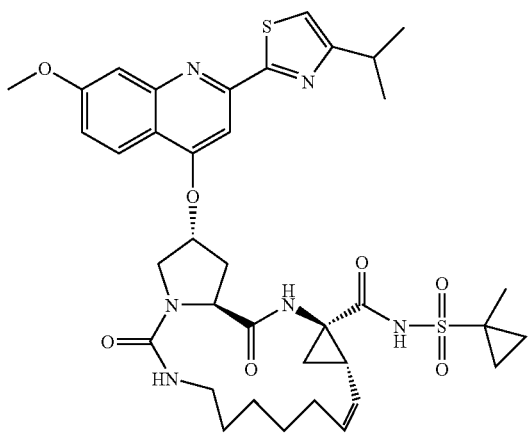

33

Step A: Preparation of 1-[[1-[Hept-6-enyl-(4-methoxybenzyl)-carbamoyl]-4-[2-(4-iso-propylthiazol-2-yl)-7-methoxyquinolin-4-yloxy]-pyrrolidine-2-carbonyl]-amino]-2-vinyl-cyclopropanecarboxylic acid ethyl ester, with the specific stereochemistry as depicted in compound (29) below

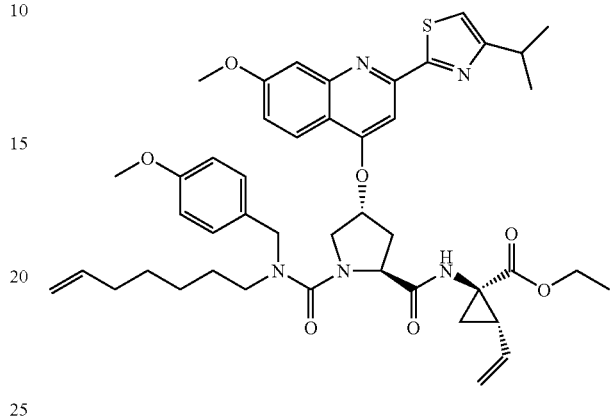

29

The title compound 29 was prepared according to the procedure described in Step A of Example 3, but using hept-6-enyl-(p-methoxybenzyl)-amine instead of hex-5-enyl-(p-methoxybenzyl)-amine.

Step B: Preparation of 18-[2-(4-Isopropylthiazol-2-yl)-7-methoxyquinolin-4-yloxy]-14-(4-methoxybenzyl)-2,15-dioxo-3,14,16-triaza-tricyclo[14.3.0.0$^{4,6}$]nonadec-7-ene-4-carboxylic acid ethyl ester, with the specific stereochemistry as depicted in compound (30) below

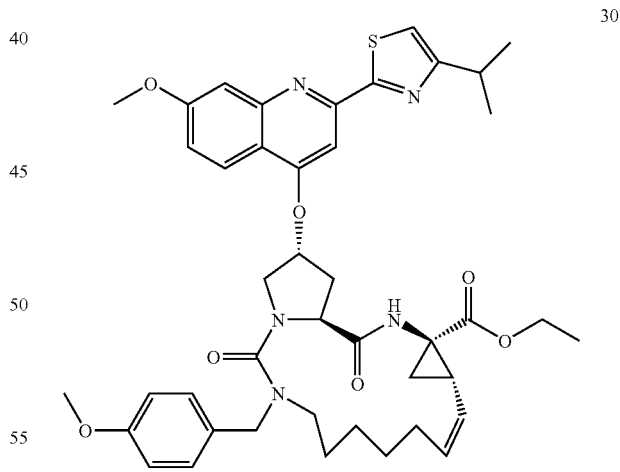

30

The compound obtained in Step A (29) was treated according to the procedure described in Step B of Example 3, which gave the title compound (30).

Step C: Preparation of 18-[2-(4-Isopropylthiazol-2-yl)-7-methoxyquinolin-4-yloxy]-14-(4-methoxybenzyl)-2,15-dioxo-3,14,16-triaza-tricyclo[14.3.0.0$^{4,6}$]nonadec-7-ene-4-carboxylic acid, with the specific stereochemistry as depicted in compound (31) below

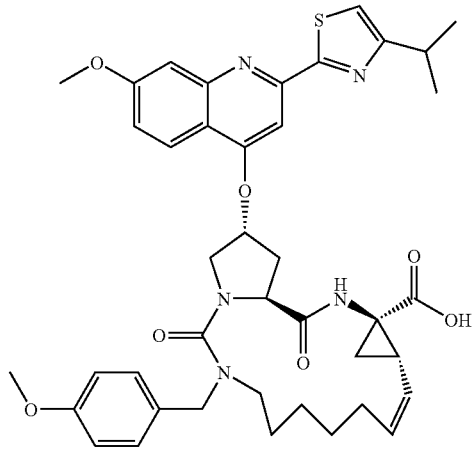

31

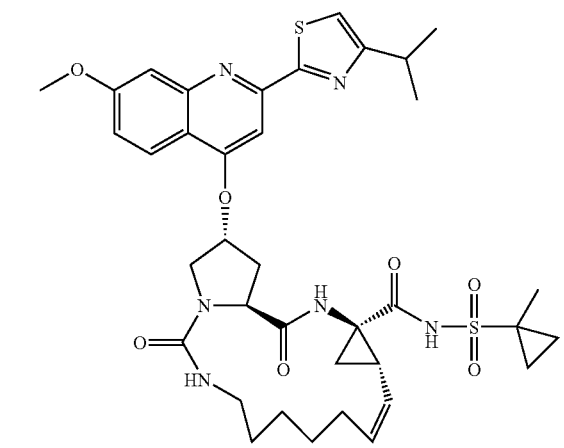

33

The compound obtained in Step B (30) was treated according to the procedure described in Step C of Example 3 which gave the title compound (31).

Step D: Preparation of 1-Methyl-cyclopropanesulphonic acid [18-[2-(4-isopropyl-thiazol-2-yl)-7-methoxyquinolin-4-yloxy]-14-(4-methoxybenzyl)-2,15-dioxo-3,14,16-triaza-tricyclo[14.3.0.0$^{4,6}$]nonadec-7-ene-4-carbonyl]-amide, with the specific stereochemistry as depicted in compound (32) below

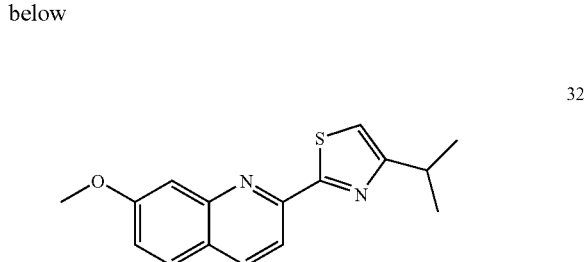

32

The compound obtained in Step C above (31) was treated according to the procedure described in Step D of Example 3, but using LiHMDS as base instead of DBU (4 eq, 1M solution in THF). The reaction was complete after 2 h at room temperature. The title compound (32) was obtained as a white solid after purification by column chromatography on silica, and was used in the next step without additional purification.

Step E: Preparation of 1-Methyl-cyclopropanesulphonic acid [18-[2-(4-isopropyl-thiazol-2-yl)-7-methoxyquinolin-4-yloxy]-2,15-dioxo-3,14,16-triaza-tricyclo-[14.3.0.0$^{4,6}$]nonadec-7-ene-4-carbonyl]-amide, with the specific stereochemistry as depicted in compound (33) below The compound obtained in Step D above (32) (100 mg) was treated according to the procedure described in Step E of Example 3, which gave the title compound (33) (55 mg, 73%).

Example 6

Activity of Compounds of Formula (I)

Replicon Assay

The compounds of formula (I) were examined for activity in the inhibition of HCV RNA replication in a cellular assay. The assay demonstrated that the compounds of formula (I) exhibited activity against HCV replicons functional in a cell culture. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct is bordered by 5' and 3' NTRs (non-translated regions) from HCV type 1b. Continued culture of the replicon cells in the presence of G418 (neo$^R$) is dependent on the replication of the HCV RNA. The stably transfected replicon cells that express HCV RNA, which replicates autonomously and to high levels, encoding inter alia luciferase, are used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. $EC_{50}$ values were then calculated, which value represents the amount of the compound required to decrease by 50% the level of detected luciferase activity, or more specifically, the ability of the genetically linked HCV replicon RNA to replicate.

Inhibition Assay

The aim of this in vitro assay was to measure the inhibition of HCV NS3/4A protease complexes by the compounds of the present invention. This assay provides an indication of how effective compounds of the present invention would be in inhibiting HCV NS3/4A proteolytic activity.

The inhibition of full-length hepatitis C NS3 protease enzyme was measured essentially as described in Poliakov, 2002 Prot Expression & Purification 25 363 371. Briefly, the hydrolysis of a depsipeptide substrate, Ac-DED(Edans)EEA-buψ[COO]ASK(Dabcyl)-NH$_2$ (SEQ ID NO: 1) (AnaSpec, San José, USA), was measured spectrofluorometrically in the presence of a peptide cofactor, KKGSVVIVGRIVLSGK (SEQ ID NO: 2) (Åke Engström, Department of Medical Biochemistry and Microbiology, Uppsala University, Sweden). [Landro, Biochemistry, 1997, 36(31): 9340-9348]. The enzyme (1 nM) was incubated in 50 mM HEPES, pH 7.5, 10 mM DTT, 40% glycerol, 0.1% n-octyl-D-glucoside, with 25 µM NS4A cofactor and inhibitor at 30° C. for 10 min, whereupon the reaction was initiated by addition of 0.5 µM substrate. Inhibitors were dissolved in DMSO, sonicated for 30 sec. and vortexed. The solutions were stored at −20° C. between measurements.

The final concentration of DMSO in the assay sample was adjusted to 3.3%. The rate of hydrolysis was corrected for inner filter effects according to published procedures. [Liu, 1999 Analytical Biochemistry 267 331-335]. Ki values were estimated by non-linear regression analysis (GraFit, Erithacus Software, Staines, MX, UK), using a model for competitive inhibition and a fixed value for Km (0.15 µM). A minimum of two replicates was performed for all measurements.

The following Table 1 lists compounds that were prepared according to any one of the above examples. The activities of the compounds tested are also depicted.

TABLE 1

| Example nr. | Compound nr. | $EC_{50}$ (µM) Replicon assay | Ki (nM) Enzymatic assay |
|---|---|---|---|
| Example 1 | 9 | $7.0 \times 10^{-3}$ | 0.12 |
| Example 2 | 16 | $5.5 \times 10^{-2}$ | 0.45 |
| Example 3 | 26 | $6.4 \times 10^{-3}$ | 0.4 |
| Example 4 | 28 | $2.3 \times 10^{-3}$ | 0.3 |
| Example 5 | 33 | $3.6 \times 10^{-3}$ | 0.3 |

Example 7

Permeability of Compounds of Formula (I)

This example measures the transport of compounds of formula (I) through the cells of the human gastroenteric canal. The assay uses the well known Caco-2 cells with a passage number between 40 and 60.

Apical (A) to Basolateral (B) Transport

Every compound was tested in 2-4 wells. The basolateral and the apical wells contained 1.5 mL and 0.4 mL of transport buffer (TB), respectively, and the standard concentration of the tested substances was 10 µM. Furthermore all test solutions and buffers contained 1% DMSO. Prior to the experiment the transport plates were pre-coated with culture medium containing 10% serum for 30 minutes to avoid non-specific binding to plastic material. After 21 to 28 days in culture on filter supports the cells were ready for permeability experiments.

Transport plate no. 1 comprised 3 rows of 4 wells each. Row 1 was denoted "Wash", row 2 "30 minutes" and row 3 "60 minutes". Transport plate no. 2 comprised 3 rows of 4 wells, one denoted row 4 "90 minutes", row 5 "120 minutes" and the remaining row unassigned.

The culture medium from the apical wells was removed and the inserts were transferred to a wash row (No. 1) in a transport plate (plate no. 1) out of 2 plates without inserts, which had already been prepared with 1.5 mL transport buffer (HBSS, 25 mM HEPES, pH 7.4) in rows 1 to 5. In A→B screening the TB in the basolateral well also contained 1% Bovine Serum Albumin.

0.5 mL transport buffer (HBSS, 25 mM MES, pH 6.5) was added to the inserts and the cell monolayers equilibrated in the transport buffer system for 30 minutes at 37° C. in a polymix shaker. After being equilibrated to the buffer system the Transepithelial electrical resistance value (TEER) was measured in each well by an EVOM chop stick instrument. The TEER values were usually between 400 and 1000 S2 per well (depending on the passage number used).

The transport buffer (TB, pH 6.5) was removed from the apical side and the insert was transferred to the 30 minutes row (No. 2) and fresh 425 µL TB (pH 6.5), including the test substance was added to the apical (donor) well. The plates were incubated in a polymix shaker at 37° C. with a low shaking velocity of approximately 150 to 300 rpm. After 30 minutes incubation in row 2 the inserts were moved to new pre-warmed basolateral (receiver) wells every 30 minutes; row 3 (60 minutes), 4 (90 minutes) and 5 (120 minutes).

25 µL samples were taken from the apical solution after ~2 minutes and at the end of the experiment. These samples represented donor samples from the start and the end of the experiment. 300 µL were taken from the basolateral (receiver) wells at each scheduled time point and the post value of TEER was measured at the end of the experiment. To all collected samples acetonitrile was added to a final concentration of 50% in the samples. The collected samples were stored at −20° C. until analysis by HPLC or LC-MS.

Basolateral to Apical Transport

Every compound was tested in 2-4 wells. The basolateral and the apical wells contained 1.55 mL and 0.4 mL TB, respectively, and the standard concentration of the tested substances was 10 Furthermore all test solutions and buffers contained 1% DMSO. Prior to the experiment the transport plates were pre-coated with culture medium containing 10% serum for 30 minutes to avoid nonspecific binding to plastic material.

After 21 to 28 days in culture on filter supports, the cells were ready for permeability experiments. The culture medium from the apical wells was removed and the inserts were transferred to a wash row (No. 1) in a new plate without inserts (Transport plate). The transport plate comprised 3 rows of 4 wells. Row 1 was denoted "wash" and row 3 was the "experimental row". The transport plate had previously been prepared with 1.5 mL TB (pH 7.4) in wash row No. 1 and with 1.55 mL TB (pH 7.4), including the test substance, in experimental row No. 3 (donor side).

0.5 mL transport buffer (HBSS, 25 mM MES, pH 6.5) was added to the inserts in row No. 1 and the cell monolayers were equilibrated in the transport buffer system for 30 minutes, 37° C. in a polymix shaker. After being equilibrated to the buffer system the TEER value was measured in each well by an EVOM chop stick instrument.

The transport buffer (TB, pH 6.5) was removed from the apical side and the insert was transferred to row 3 and 400 µL fresh TB, pH 6.5 was added to the inserts. After 30 minutes 250 µL was withdrawn from the apical (receiver) well and replaced by fresh transport buffer. Thereafter 250 µL samples were withdrawn and replaced by fresh transport buffer every 30 minutes until the end of the experiment at 120 minutes, and finally a post value of TEER was measured at the end of the experiment. A 25 sample was taken from the basolateral (donor) compartment after ~2 minutes and at the end of the experiment. These samples represented donor samples from the start and the end of the experiment.

To all collected samples acetonitrile was added to a final concentration of 50% in the samples. The collected samples were stored at −20° C. until analysis by HPLC or LC-MS.

Determination of the cumulative fraction absorbed, $FA_{cum}$, versus time. $FA_{cum}$ was calculated from:

$$FA_{cum} = \sum \frac{C_{RI}}{C_{DI}}$$

where $C_{Ri}$ is the receiver concentration at the end of the interval i and $C_{Di}$ is the donor concentration at the beginning of interval i. A linear relationship should be obtained.

The determination of permeability coefficients ($P_{app}$, cm/s) were calculated from:

$$P_{app} = \frac{(k \cdot V_R)}{(A \cdot 60)}$$

where k is the transport rate (min$^{-1}$) defined as the slope obtained by linear regression of cumulative fraction absorbed ($FA_{cum}$) as a function of time (min), $V_R$ is the volume in the receiver chamber (mL), and A is the area of the filter (cm$^2$).

TABLE 2

| Reference compounds | | |
|---|---|---|
| Category of absorption in man | Markers | % absorption in man |
| PASSIVE TRANSPORT | | |
| Low (0-20%) | Mannitol | 16 |
| | Methotrexate | 20 |
| Moderate (21-75%) | Acyclovir | 30 |
| High (76-100%) | Propranolol | 90 |
| | Caffeine | 100 |
| ACTIVE TRANSPORT | | |
| Amino acid transporter | L-Phenylalanine | 100 |
| ACTIVE EFFLUX | | |
| PGP-MDR1 | Digoxin | 30 |

The following table 3 shows the permeability results ($P_{app}$) expressed in 10$^{-6}$ cm/s for a representative selection of compounds according to the invention when tested in the permeability assay described above.

TABLE 3

| Compound No. | $P_{app}$ (10$^{-6}$ cm/s) |
|---|---|
| 9 | 11 |
| 26 | 3.6 |
| 28 | 8.6 |
| 33 | 31 |

Example 8

In Vitro Metabolic Blocking of Hcv Ns3/4a Protease Inhibitors by Ritonavir

Different HCV NS3/4a protease inhibitors were tested in a metabolic blocking experiment using 3 µM test compound together with 10 µM ritonavir acting as booster. Test compounds and ritonavir were added to human liver microsomes (protein concentration 1 mg/ml) suspended in potassium phosphate buffer (pH=7.4), to get final reaction mixture concentrations of 3 µM test compound and 10 µM ritonavir. In the non-boosted parallel reactions, ritonavir was not added. Boiled human liver microsomes were used for blank experiments. After addition (in a 1:3 ratio) of a cofactor mixture consisting of β-nicotinamide adenine dinucleotide phosphate (β-NADP, 0.5 mg/ml, 653.2 µM), D-Glucose-6-phosphate (2 mg/ml, 7.1 mM), Glucose-6-phosphate dehydrogenase (1.5 U/ml) in 2% NaHCO$_3$, the reaction mixture was incubated at 37° C. for 30 or 120 minutes after which the reaction was stopped by increasing the temperature to 95° C. Test compound concentrations were determined using HPLC-MS.

Results are summarized in the table 4 below. Values are percentages of test compound detected after the indicated incubation times as compared to the initial test compound concentration. Each value is the mean of the results of two independent experiments.

TABLE 4

| | 30' % Detected Compound | | 120' % Detected Compound | |
|---|---|---|---|---|
| Compound nr. | No Booster | ritonavir | No Booster | ritonavir |
| 16 | 71 | 93 | 20 | 102 |
| 9 | 44 | 88 | 0 | 100 |

The experiment shows an almost complete blocking of test compound (3 µM) metabolisation by addition of 10 µM ritonavir.

Example 9

In Vivo Effects of Ritonavir on the Pharmacokinetics of Compound Nr. 9 in Dog

Oral pharmacokinetics of Compound nr. 9 in male Beagle dogs after a single dose at 10 mg/kg, using a formulation in 50% PEG400/water and the influence of "boosting" with 10 mg/kg ritonavir were investigated.

Six male Beagle dogs (body weight 8-10 kg) were randomly divided into 2 groups of 3 animals (boosted and non-boosted). No untreated or vehicle-treated control animals were included. Before dosing, the animals were fasted overnight (approx. 12 h fasting period) and did not receive any food before dosing until 6 hours after dosing. Drinking water remained available throughout the experiment.

Dogs from the non-boosted group received a single oral 10 mg/kg dose of Compound nr. 9, formulated as a 5 mg/ml 50% PEG400/water. Dogs from the boosted group received a single soft capsule of Norvir® (ritonavir, 100 mg/capsule), about 30 minutes before single oral dosing with 10 mg/kg of Compound nr. 9. The drug formulations were administered by oral gavage, using a gastric tube.

A 3 ml blood sample was collected at 0.5 h 1 h, 2 h, 4 h, 6 h, 8 h and 24 hours after dosing of Compound nr. 9. Plasma concentrations were determined using HPLC-MS. Results are shown in the table 5 below, expressed as fold change in pharmacokinetic parameter of the boosted group as compared to the non-boosted group.

TABLE 5

| pharmacokinetic parameter | Fold increase in compound nr 9 when boosted with ritonavir |
|---|---|
| $C_{max}$ | 31 |
| AUC | 55 |

These results demonstrate that ritonavir substantially enhances the pharmacokinetics of Compound nr. 9 in dog, with overall exposures expressed as AUC increasing 55-fold.

The invention claimed is:

1. A compound having the formula

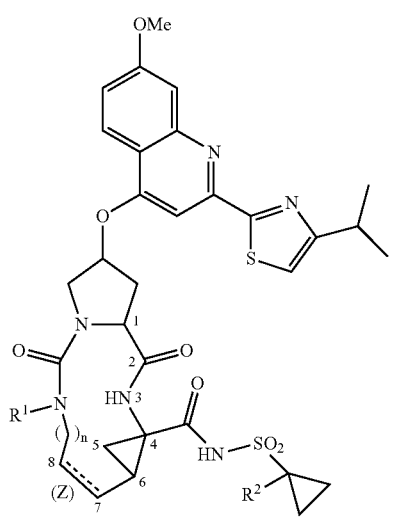

and the N-oxides, salts, and stereoisomers thereof, wherein the dashed line represents an optional double bond between atoms C7 and C8;

$R^1$ is hydrogen or $C_{1-6}$alkyl;
$R^2$ is hydrogen or $C_{1-6}$alkyl; and
n is 3, 4, 5, or 6.

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Abu

<400> SEQUENCE: 1

Asp Glu Asp Glu Glu Xaa
1               5

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Lys Gly Ser Val Val Ile Val Gly Arg Ile Val Leu Ser Gly Lys
1               5                   10                  15
```

2. The compound according to claim 1, wherein the compound has the formula (I-a):

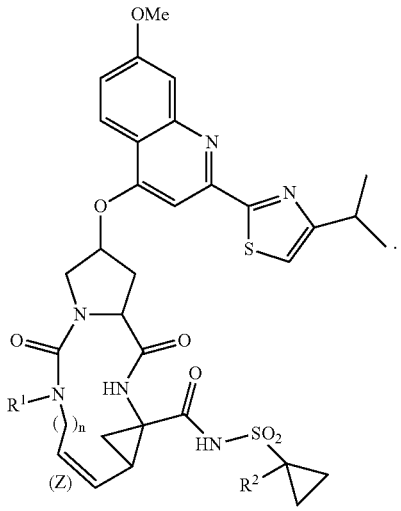

(I-a)

3. The compound of claim 1, wherein the compound has the formula (I-b):

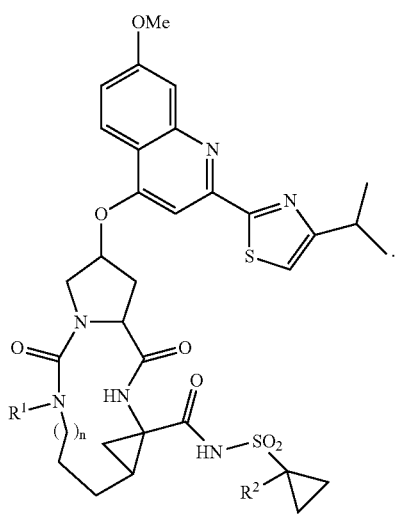

(I-b)

4. The compound of claim 1, wherein n is 4 or 5.
5. The compound of claim 1, wherein $R^1$ is hydrogen or methyl.
6. The compound of claim 1, wherein $R^2$ is hydrogen.
7. The compound of claim 1, wherein $R^2$ is methyl.

8. The compound of claim 1, wherein the compound is selected from

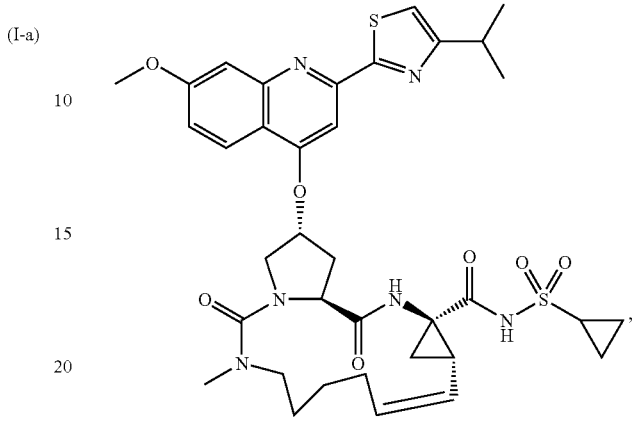

16

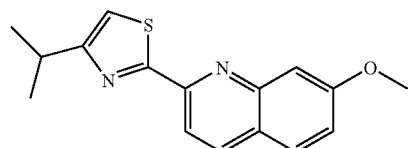

,

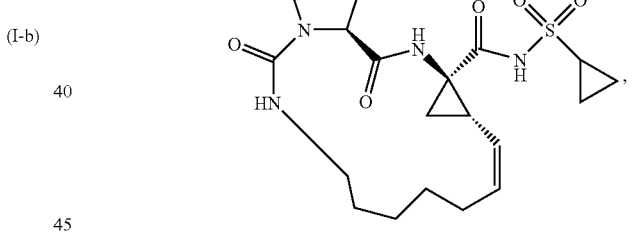

9

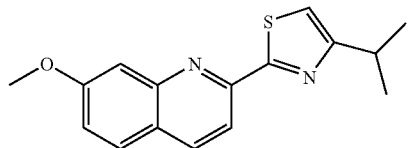

,

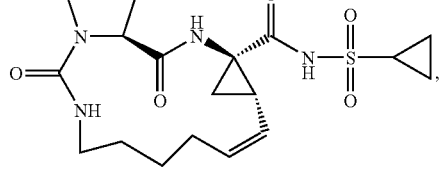

26

,

-continued

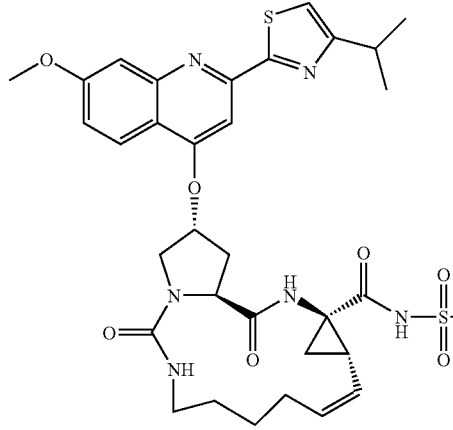

28

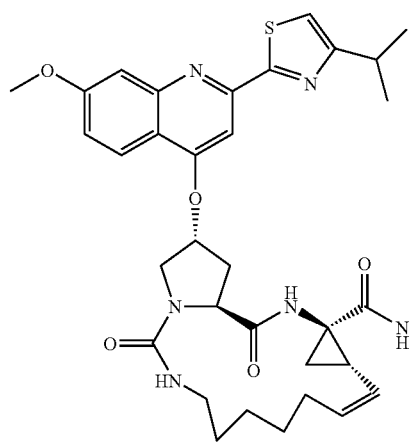

33

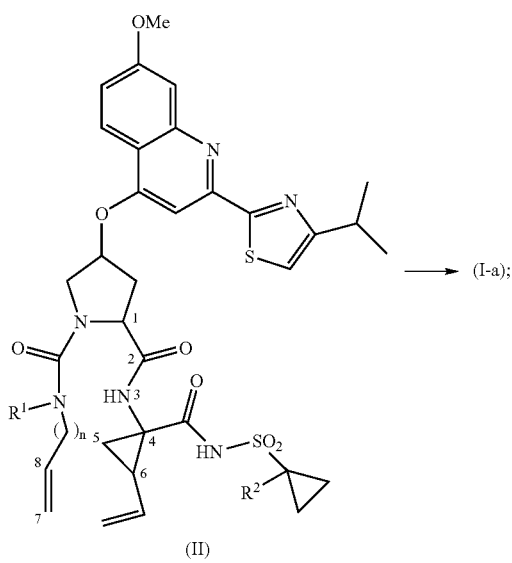

(II)

(b) converting a compound of formula (I-a) to a compound of formula (I) wherein the link between C7 and C8 in the macrocycle is a single bond, i.e. a compound of formula (I-b)

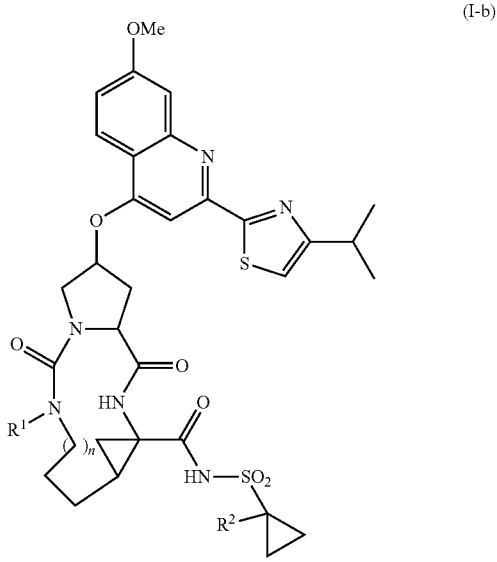

(I-b)

wherein $R^1$ and $R^2$ are as defined in claim 1, by a reduction of the C7-C8 double bond in the compound of formula (I-a);

(c) reacting a cyclopropylsulfonamide (IV) with an intermediate (III) via an amide forming reaction as outlined in the following reaction scheme:

9. The compound of claim 1 other than an N-oxide or salt.

10. A combination comprising (a) a compound as defined in claim 1 or a pharmaceutically acceptable salt thereof; and (b) ritonavir, or a pharmaceutically acceptable salt thereof.

11. A pharmaceutical composition comprising a carrier, and as active ingredient an anti-virally effective amount of the compound of claim 1.

12. A method of inhibiting HCV replication in a warm-blooded animal, said method comprising administering an effective amount of the compound of claim 1.

13. A process for preparing a compound of claim 1, wherein said process comprises:

(a) preparing a compound of formula (I) wherein the bond between $C_7$ and $C_8$ is a double bond, which is a compound of formula (I-a), by forming of a double bond between $C_7$ and $C_8$, via an olefin metathesis reaction, with concomitant cyclization to the macrocycle as outlined in the following reaction scheme:

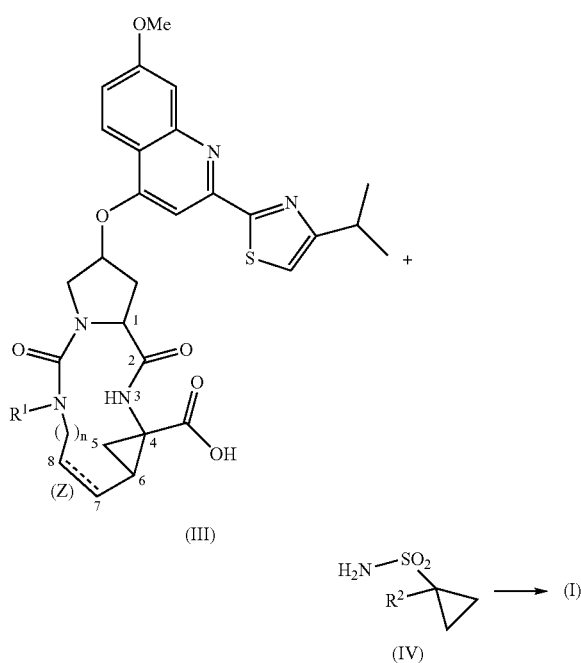

(III)

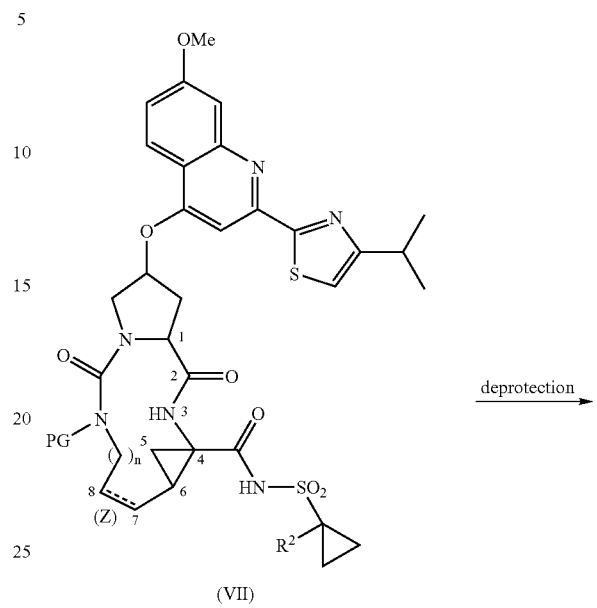

(d) etherifying an intermediate (V) with a quinoline of formula (VI) as outlined in the following reaction scheme:

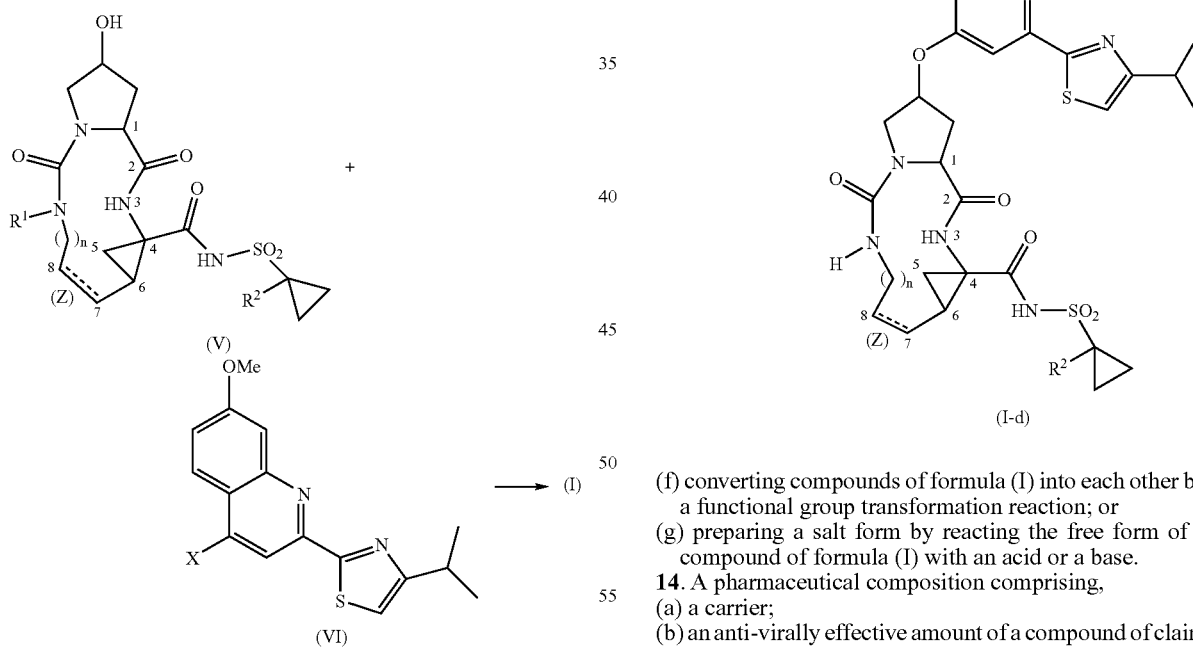

wherein X in (VI) represents hydroxy or a leaving group; which reaction is an O-arylation reaction wherein X represents a leaving group, or a Mitsunobu reaction, wherein X is hydroxy;

(e) preparing a compound of formula (I) wherein $R^1$ is hydrogen, said compound being represented by (I-d), from a corresponding nitrogen-protected intermediate (VII), wherein PG represents a nitrogen protecting group:

(f) converting compounds of formula (I) into each other by a functional group transformation reaction; or (g) preparing a salt form by reacting the free form of a compound of formula (I) with an acid or a base.

14. A pharmaceutical composition comprising,
(a) a carrier;
(b) an anti-virally effective amount of a compound of claim 1 or a pharmaceutically acceptable salt thereof; and
(c) ritonavir, or a pharmaceutically acceptable salt thereof.

15. A method of inhibiting HCV replication in a warm-blooded animal, said method comprising administering:
(a) a compound of claim 1 or a pharmaceutically acceptable salt thereof; and
(b) ritonavir, or a pharmaceutically acceptable salt thereof.

* * * * *